(12) United States Patent
Kaneko

(10) Patent No.: US 9,517,013 B2
(45) Date of Patent: Dec. 13, 2016

(54) IMAGE PROCESSING APPARATUS, MICROSCOPE SYSTEM, ENDOSCOPE SYSTEM, AND IMAGE PROCESSING METHOD

(71) Applicant: OLYMPUS CORPORATION, Tokyo (JP)

(72) Inventor: Yoshioki Kaneko, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 71 days.

(21) Appl. No.: 14/565,960

(22) Filed: Dec. 10, 2014

(65) Prior Publication Data

US 2015/0119722 A1   Apr. 30, 2015

Related U.S. Application Data

(63) Continuation of application No. PCT/JP2013/062648, filed on Apr. 30, 2013.

(30) Foreign Application Priority Data

Jun. 15, 2012   (JP) .................................. 2012-136377

(51) Int. Cl.
*G06K 9/00* (2006.01)
*A61B 5/00* (2006.01)
(Continued)

(52) U.S. Cl.
CPC ......... *A61B 5/0071* (2013.01); *A61B 1/00009* (2013.01); *A61B 1/043* (2013.01);
(Continued)

(58) Field of Classification Search
CPC ... A61B 5/4227; A61B 5/0071; A61B 1/0661;
A61B 1/043; G02B 21/365; G02B 21/16;
G02B 2207/113; G01N 21/6458; G01N
21/6486; G01N 2201/0826
(Continued)

(56) References Cited

U.S. PATENT DOCUMENTS 6,258,576 B1   7/2001   Richards-Kortum et al.
6,326,201 B1 *  12/2001   Fung .................... C12N 5/0678
                                              435/325
(Continued)

FOREIGN PATENT DOCUMENTS

JP   2001501727 A   2/2001
JP   2003533674 A   11/2003
(Continued)

OTHER PUBLICATIONS

International Search Report dated Aug. 6, 2013 issued in PCT/JP2013/062648.
(Continued)

*Primary Examiner* — Ali Bayat
(74) *Attorney, Agent, or Firm* — Scully, Scott, Murphy & Presser, P.C.

(57) ABSTRACT

An image processing apparatus includes: an image acquiring unit configured to acquire image information representing an image acquired by irradiating a gland duct with excitation light and observing fluorescence generated in the gland duct; a fluorescence intensity computation unit configured to compute a value corresponding to intensity of the fluorescence as fluorescence intensity based on the image information; and an image determination unit configured to determine whether or not an endocrine cell exists in the gland duct based on the fluorescence intensity computed by the fluorescence intensity computation unit, and to determine abnormality of the gland duct based on a determination result of the endocrine cell.

19 Claims, 29 Drawing Sheets

(51) Int. Cl.

| | |
|---|---|
| *G02B 21/16* | (2006.01) |
| *G02B 21/36* | (2006.01) |
| *G01N 21/64* | (2006.01) |
| *G06T 7/00* | (2006.01) |
| *A61B 1/06* | (2006.01) |
| *A61B 1/00* | (2006.01) |
| *A61B 1/04* | (2006.01) |

(52) U.S. Cl.
CPC ............ *A61B 1/0661* (2013.01); *A61B 5/415* (2013.01); *A61B 5/4227* (2013.01); *G01N 21/6456* (2013.01); *G01N 21/6458* (2013.01); *G01N 21/6486* (2013.01); *G02B 21/16* (2013.01); *G02B 21/365* (2013.01); *G06T 7/0012* (2013.01); *G01N 2021/6417* (2013.01); *G01N 2021/6484* (2013.01); *G01N 2201/0826* (2013.01); *G02B 2207/113* (2013.01); *G06T 2207/10068* (2013.01); *G06T 2207/30024* (2013.01)

(58) Field of Classification Search
USPC .......................................................... 382/128
See application file for complete search history.

(56) References Cited

U.S. PATENT DOCUMENTS

| | | | |
|---|---|---|---|
| 6,364,829 B1 | 4/2002 | Fulghum | |
| 6,405,070 B1 | 6/2002 | Banerjee | |
| 6,405,074 B1 | 6/2002 | Banerjee | |
| 6,537,211 B1 | 3/2003 | Wang et al. | |
| 6,946,293 B1* | 9/2005 | Lu ........................ | C12N 5/0678 435/325 |
| 8,594,411 B2 | 11/2013 | Yoshihara et al. | |
| 2002/0161282 A1 | 10/2002 | Fulghum | |
| 2003/0055341 A1 | 3/2003 | Banerjee | |
| 2003/0191368 A1 | 10/2003 | Wang et al. | |
| 2004/0038320 A1 | 2/2004 | Banerjee | |
| 2004/0162489 A1 | 8/2004 | Richards-Kortum et al. | |
| 2008/0113911 A1* | 5/2008 | Kuo ................... | A61K 38/1709 514/1.9 |
| 2008/0317722 A1* | 12/2008 | Rohrschneider ......... | C12N 9/16 424/93.21 |
| 2011/0213252 A1 | 9/2011 | Fulghum | |
| 2012/0082365 A1 | 4/2012 | Yoshihara et al. | |
| 2012/0195869 A1* | 8/2012 | Terman .................. | A61K 35/18 424/93.73 |
| 2013/0224756 A1* | 8/2013 | Cohen .................. | C07K 14/195 435/6.17 |
| 2015/0024458 A1* | 1/2015 | Chang .............. | A61K 47/48415 435/188 |

FOREIGN PATENT DOCUMENTS

| | | |
|---|---|---|
| JP | 2006208339 A | 8/2006 |
| JP | 2008005984 A | 1/2008 |
| JP | 2011196873 A | 10/2011 |
| JP | 2011206546 A | 10/2011 |
| WO | 2010/140588 A1 | 12/2010 |
| WO | 2010140654 A1 | 12/2010 |

OTHER PUBLICATIONS

Matsui, et al., "Jobu Shokakan Shuyo Naishikyo Shindangaku no Shinjidai 9. Soki Igan no Shindangaku-AFI ni yoru Shindangaku-", Modern Physician, Jul. 15, 2011, pp. 70-73, vol. 31, with partial English translation.

Uedo, et al., "Diagnosis of Upper Gastrointestinal Diseases Using Autofluorescence Imaging Videoendoscopy System", 2009, pp. 37-40, vol. 30, No. 1, with partial English translation.

Hanaoka, et al., "Autofluorescence imaging (AFI) ni yoru Helicobacter pylon Kansen Nenmaku no Shindan", 2011, pp. 86-92, vol. 15, No. 2, with partial English translation.

Japanese Office Action dated Sep. 20, 2016 in Japanese Patent Application No. 2014-521015.

* cited by examiner

FLUORESCENCE CUBE:U-MWU
(EXCITATION WAVELENGTHS 300nm-400nm)

FLUORESCENCE CUBE:U-MWIBA
(EXCITATION WAVELENGTHS 460nm-500nm)

FLUORESCENCE CUBE:U-MWIG
(EXCITATION WAVELENGTHS 530nm-560nm)

CELLS EMITTING FLUORESCENCE

CELLS EMITTING FLUORESCENCE

FLUORESCENCE CUBE:U-MWU
(EXCITATION WAVELENGTHS 300nm-400nm)

ENDOCRINE CELLS

FIG.21A

| AREA (NUMBER OF PIXELS) | DEGREE OF ABNORMALITY |
|---|---|
| 1000 OR MORE | 1 |
| 100 OR MORE, LESS THAN 1000 | 2 |
| 10 OR MORE, LESS THAN 100 | 3 |
| 1 OR MORE, LESS THAN 10 | 4 |
| LESS THAN 1 | 5 |

FIG.21B

| AREA (NUMBER OF PIXELS) | STAGE OF PROGRESSION |
|---|---|
| 1000 OR MORE | 0 |
| 100 OR MORE, LESS THAN 1000 | I |
| 10 OR MORE, LESS THAN 100 | II |
| 1 OR MORE, LESS THAN 10 | III |
| LESS THAN 1 | IV |

FIG.21C

| AREA (NUMBER OF PIXELS) | DEPTH OF INVASION (T CATEGORY) |
|---|---|
| 1000 OR MORE | Tis |
| 100 OR MORE, LESS THAN 1000 | T1 |
| 10 OR MORE, LESS THAN 100 | T2 |
| 1 OR MORE, LESS THAN 10 | T3 |
| LESS THAN 1 | T4 |

FIG.21D

| AREA (NUMBER OF PIXELS) | DEGREE OF METASTASIS |
|---|---|
| 1000 OR MORE | 1 |
| 100 OR MORE, LESS THAN 1000 | 2 |
| 10 OR MORE, LESS THAN 100 | 3 |
| 1 OR MORE, LESS THAN 10 | 4 |
| LESS THAN 1 | 5 |

FIG.21E

| AREA (NUMBER OF PIXELS) | DEGREE OF METASTASIS (LYMPH NODES/ N CATEGORY) |
|---|---|
| 1000 OR MORE | N0 |
| 100 OR MORE, LESS THAN 1000 | N1 |
| 10 OR MORE, LESS THAN 100 | N2 |
| 1 OR MORE, LESS THAN 10 | |
| LESS THAN 1 | |

FIG.21F

| AREA (NUMBER OF PIXELS) | DEGREE OF METASTASIS (DISTANT/M CATEGORY) |
|---|---|
| 1000 OR MORE | M0 |
| 100 OR MORE, LESS THAN 1000 | |
| 10 OR MORE, LESS THAN 100 | M1 |
| 1 OR MORE, LESS THAN 10 | |
| LESS THAN 1 | |

FIG.21G

| ROUNDNESS | DEGREE OF ABNORMALITY |
|---|---|
| 1 | 1 |
| 0.8 OR MORE, LESS THAN 1 | 2 |
| 0.6 OR MORE, LESS THAN 0.8 | 3 |
| 0.4 OR MORE, LESS THAN 0.6 | 4 |
| LESS THAN 0.4 | 5 |

| AREA (NUMBER OF PIXELS) | DEGREE OF ABNORMALITY |
|---|---|
| LESS THAN 1 | 1 |
| 1 OR MORE, LESS THAN 10 | 2 |
| 10 OR MORE, LESS THAN 100 | 3 |
| 100 OR MORE, LESS THAN 1000 | 4 |
| 1000 OR MORE | 5 |

IMAGE PROCESSING APPARATUS, MICROSCOPE SYSTEM, ENDOSCOPE SYSTEM, AND IMAGE PROCESSING METHOD

CROSS REFERENCES TO RELATED APPLICATIONS

This application is a continuation of PCT international application Ser. No. PCT/JP2013/062648 filed on Apr. 30, 2013 which designates the United States, incorporated herein by reference, and which claims the benefit of priority from Japanese Patent Application No. 2012-136377, filed on Jun. 15, 2012, incorporated herein by reference.

BACKGROUND

1. Technical Field

The disclosure relates to an image processing apparatus for processing an image showing a living body, a microscope system, an endoscope system, and an image processing method.

2. Related Art

Upon detection of an abnormality and the like of an organ of a living body, an observation method and a staining method are conventionally selected and used in accordance with an observation target and an observation purpose. For example, in a case of organs having a glandular structure, such as the esophagus, stomach, small intestine, large intestine, and prostate gland, an observation method is used in which a pathological specimen taken from a living body is stained to make microscopic observations, or an endoscope is inserted into the living body to make observations with irradiation of white light.

As an example, when an abnormality (lesion) is detected from a pathological specimen, non-fluorescent staining such as hematoxylin and eosin staining (hereinafter referred to as "HE staining") that uses two dyes of hematoxylin and eosin, or Papanicolaou stain (Pap stain) is performed first as morphological observation staining to observe the forms of tissues and cells. Bright-field observation with transmitted-light illumination is performed by an optical microscope.

Moreover, the lack of information in morphological diagnosis based on morphology information may be complemented, or staining called special staining or immunostaining for judging suitability of the administration of a drug may be performed. For example, when a molecular pathological examination for diagnosing a functional abnormality such as the abnormal expression of a molecular target (a specific gene or protein) is performed, the molecular target is fluorescence-labeled (stained) to perform fluorescence observation with epi-illumination, or is enzyme-labeled to perform bright-field observation, by an immunohistochemistry (IHC) method, an immunocytochemistry (ICC) method, an in situ hybridization (ISH) method, or the like.

In addition, various techniques are known which automatically extract an area corresponding to a diagnosis target from an image obtained by capturing a stained specimen, by image processing (see, for example, Japanese Laid-open Patent Publication No. 2006-208339).

Moreover, Japanese National Publication of International Patent Application No. 2003-533674 discloses methods in detecting abnormal cells and tissues based upon measurement of tryptophan-associated autofluorescence (intrinsic fluorescence).

SUMMARY

In accordance with some embodiments, an image processing apparatus for processing an image showing a living body, a microscope system, an endoscope system, and an image processing method are presented.

In some embodiments, an image processing apparatus includes: an image acquiring unit configured to acquire image information representing an image acquired by irradiating a gland duct with excitation light and observing fluorescence generated in the gland duct; a fluorescence intensity computation unit configured to compute a value corresponding to intensity of the fluorescence as fluorescence intensity based on the image information; and an image determination unit configured to determine whether or not an endocrine cell exists in the gland duct based on the fluorescence intensity computed by the fluorescence intensity computation unit, and to determine abnormality of the gland duct based on a determination result of the endocrine cell.

In some embodiments, an image processing apparatus includes: an image acquiring unit configured to acquire image information representing an image acquired by irradiating a gland duct with excitation light and observing fluorescence generated in the gland duct; a spectrum generation unit configured to generate an optical spectrum of each pixel in the image based on the image information; a pixel area extracting unit configured to extract an area of pixels in which the optical spectrum generated by the spectrum generation unit has a specified characteristic; and an image determination unit configured to determine whether or not an endocrine cell exists in the gland duct based on a characteristic amount of the area extracted by the pixel area extracting unit, and to determine abnormality of the gland duct based on a determination result of the endocrine cell.

In some embodiments, an image processing apparatus includes: an image acquiring unit configured to acquire image information representing an image acquired by irradiating a gland duct with excitation light and observing fluorescence generated in the gland duct; a wavelength limitation unit configured to generate a wavelength limited image in which a wavelength component of each pixel in the image is limited to a specified wavelength band; a pixel area extracting unit configured to extract an area of pixels having a luminance value that is a specified value or more from the wavelength limited image generated by the wavelength limitation unit; and an image determination unit configured to determine whether or not an endocrine cell exists in the gland duct based on a characteristic amount of the area extracted by the pixel area extracting unit, and to determine abnormality of the gland duct based on a determination result of the endocrine cell.

In some embodiments, a microscope system includes: the above-described image processing apparatus; a stage on which a specimen is to be placed; an illumination optical system configured to apply excitation light to the stage; an objective optical system provided facing the stage to allow light from a direction of the specimen to be incident thereon; and an imaging unit configured to capture observation light of the specimen which has passed through the objective optical system, and to generate image information.

In some embodiments, an endoscope system includes: the above-described image processing apparatus; an illumination optical system configured to apply excitation light to a specimen; an objective optical system provided facing the specimen to allow light from a direction of the specimen to be incident thereon; and an imaging unit configured to capture observation light of the specimen which has passed through the objective optical system, and to generate image information.

In some embodiments, an image processing method includes: an image acquiring step of acquiring image information representing an image acquired by irradiating a gland duct with excitation light and by observing fluorescence generated in the gland duct; a fluorescence intensity computation step of computing a value corresponding to intensity of the fluorescence as fluorescence intensity based on the image information; and an image determination step of determining whether or not an endocrine cell exists in the gland duct based on the fluorescence intensity computed in the fluorescence intensity computation step, and determining abnormality of the gland duct based on a determination result of the endocrine cell.

The above and other features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 21A is a lookup table in which the area (number of pixels) of a fluorescence area is associated with the degree of abnormality of the mucosa of the large intestine;

FIG. 21B is a lookup table in which the area (number of pixels) of a fluorescence area is associated with the stage of cancer;

FIG. 21C is a lookup table in which the area (number of pixels) of a fluorescence area is associated with the depth of cancer invasion (T category);

FIG. 21D is a lookup table in which the area (number of pixels) of a fluorescence area is associated with the degree of cancer metastasis;

FIG. 21E is a lookup table in which the area (number of pixels) of a fluorescence area is associated with the degree of cancer metastasis (lymph nodes/N category);

FIG. 21F is a lookup table in which the area (number of pixels) of a fluorescence area is associated with the degree of cancer metastasis (distant metastasis/M category);

FIG. 21G is a lookup table in which the roundness of a fluorescence area is associated with the degree of abnormality of the mucosa of the large intestine;

DETAILED DESCRIPTION

Hereinafter, embodiments of an image processing apparatus, a microscope system, an endoscope system, and an image processing method according to the present invention will be described in detail with reference to the drawings. The present invention is not limited by these embodiments. Moreover, the same reference signs are used to refer to the same elements throughout the drawings.

First Embodiment

Figure 1:
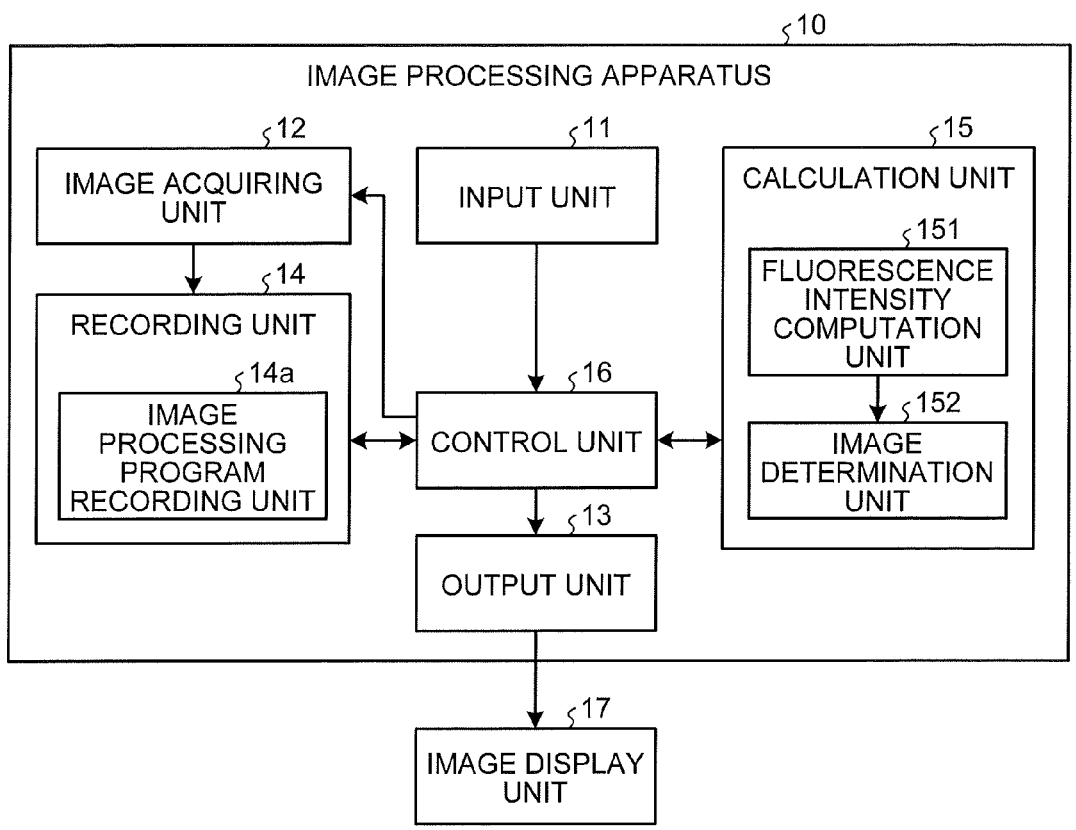
FIG. 1 is a block diagram illustrating the configuration of an image processing apparatus according to a first embodiment of the present invention.

FIG. 1 is a diagram illustrating the configuration of an image processing apparatus according to a first embodiment of the present invention. Moreover, FIG. 2 to FIG. 8 are diagrams and images for illustrating an outline of image processing in the present invention. Firstly, the outline of image processing in the present invention is described with reference to FIG. 2 to FIG. 8.

The embodiments described below relate to an image processing apparatus that determines the abnormality of a gland duct based on a fluorescence observation image of the unstained gland duct, a microscope system, an endoscope system, and an image processing method. The gland duct here is a generic name for portions forming the mucosal epithelia of a living body such as the large intestine, stomach, small intestine, esophagus, prostate gland, pancreas, lungs, mammary gland, and ovaries.

Figure 2:
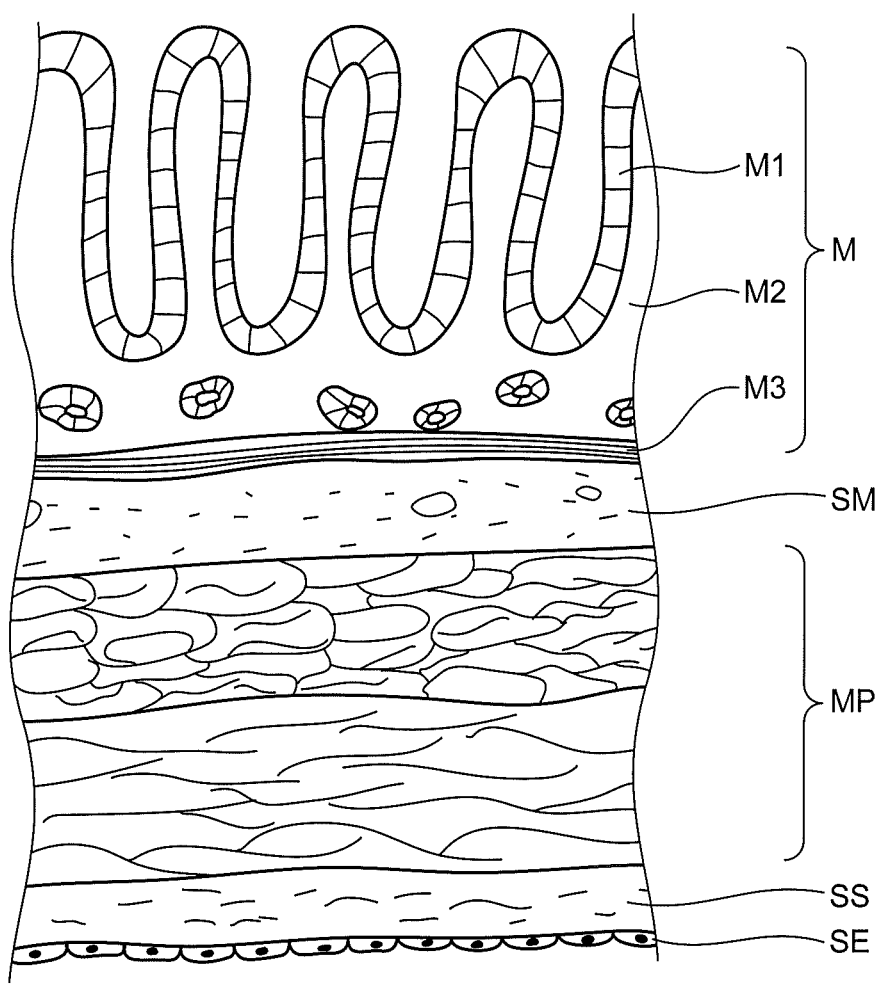
FIG. 2 is a schematic diagram illustrating a cross section of tissues in the vicinity of the mucosa of the large intestine.

FIG. 2 is a schematic diagram illustrating a cross section of tissues in the vicinity of the mucosa of the large intestine. The mucosa of the large intestine includes the mucosa M, the submucosa SM, the muscularis propria MP, the subserosa SS, and the serosa SE from the surface side. Of them, the mucosa M includes three kinds of tissues of the epithelium M1, the lamina propria M2, and the muscularis mucosae M3.

FIG. 3 to FIG. 6 are images acquired by observing the fluorescence of unstained specimens of such mucosae of the large intestine. The specimens are created by paraffin embedding normal mucosal tissue of the large intestine, cutting thin slices of the tissue with a microtome, and fixing the tissue on a glass slide, bonding a cover glass using a mounting medium while the tissue is not stained (is unstained). The specimen is set on an epi-illumination fluorescence microscope, and captured by a CCD camera that can capture an image in a wavelength band of 400 nm to 700 nm, using a fluorescence cube that can transmit observation light (fluorescence) in a specified wavelength band from the specimen, while being irradiated with excitation light in a specified wavelength band.

Figure 3:
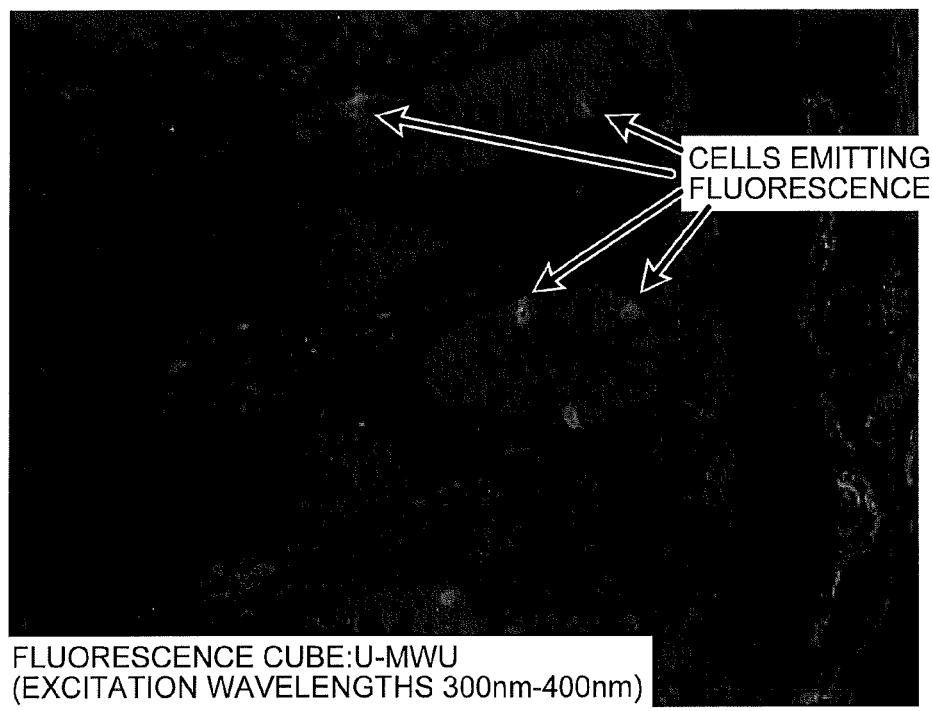
FIG. 3 is a fluorescence observation image (excitation wavelengths of 300 nm to 400 nm, and imaging wavelengths of 400 nm to 700 nm) of an unstained specimen of the mucosa of the large intestine.

FIG. 3 is a fluorescence observation image in a wavelength band of the excitation light (excitation wavelengths) of 300 nm to 400 nm, and imaging wavelengths of 400 nm to 700 nm. A U-MWU cube made by Olympus Corporation was used as a fluorescence cube. In FIG. 3, cells emitting strong fluorescence (appearing green during the experiment) were specifically observed in the epithelium M1 (appearing blue during the experiment) displayed over the image. The cells can also be distinguished from other areas from the difference in color (in other words, the optical spectrum) in addition to the fluorescence intensity.

When the same specimen was observed with the same field of view in bright field, the tissues could hardly be visible since the specimen was unstained. The existence of the cells emitting fluorescence could not be confirmed either.

Figure 4:
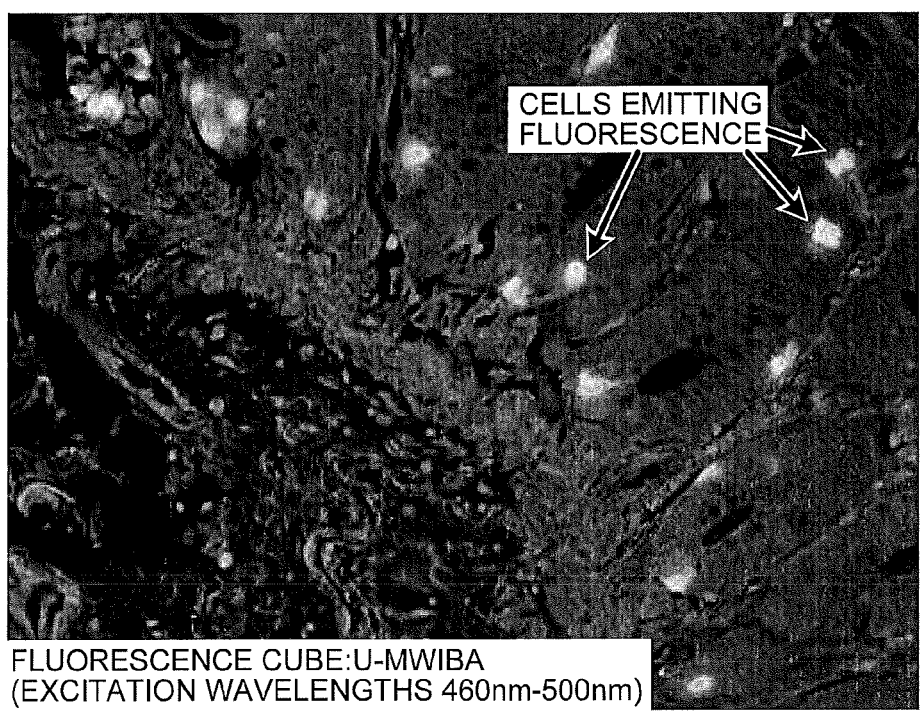
FIG. 4 is a fluorescence observation image (excitation wavelengths of 460 nm to 500 nm, and imaging wavelengths of 510 nm to 550 nm) of an unstained specimen of the mucosa of the large intestine.

FIG. 4 is a fluorescence observation image in a wavelength band of the excitation light of 460 nm to 500 nm, and imaging wavelengths of 510 nm to 550 nm. A U-MWIBA cube made by Olympus Corporation was used as a fluorescence cube. In this case, the entire image appeared greenish. Cells emitting strong fluorescence were specifically observed in the epithelium M1.

Figure 5:
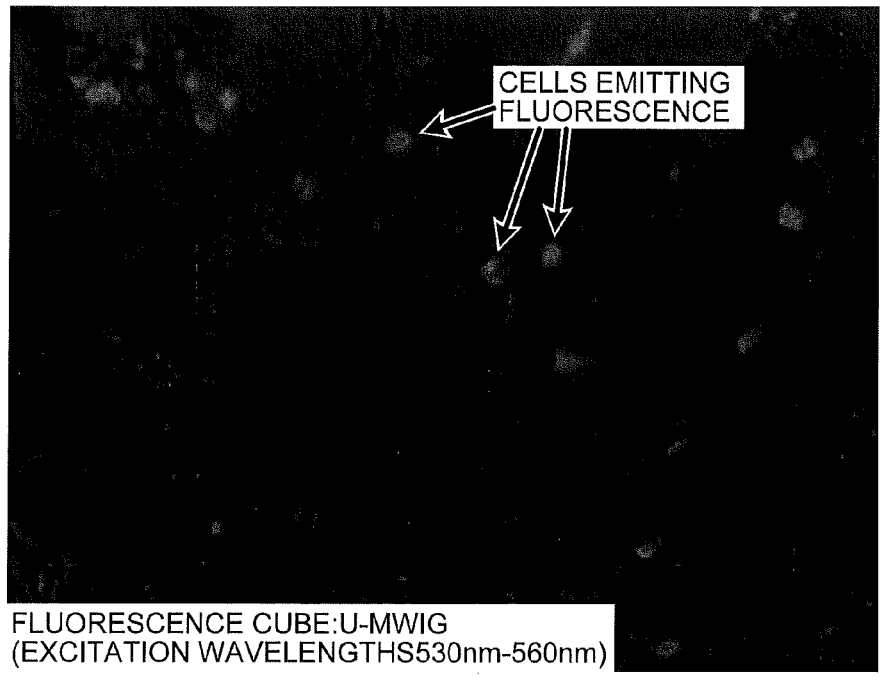
FIG. 5 is a fluorescence observation image (excitation wavelengths of 530 nm to 560 nm, and imaging wavelengths of 570 nm to 700) of an unstained specimen of the mucosa of the large intestine.

FIG. 5 is a fluorescence observation image in a wavelength band of the excitation light of 530 nm to 560 nm, and imaging wavelengths of 570 nm to 700 nm. A U-MWIG cube made by Olympus Corporation was used as a fluorescence cube. In this case, the entire image appeared orangish. Cells emitting strong fluorescence were specifically observed in the epithelium M1.

Figure 6:
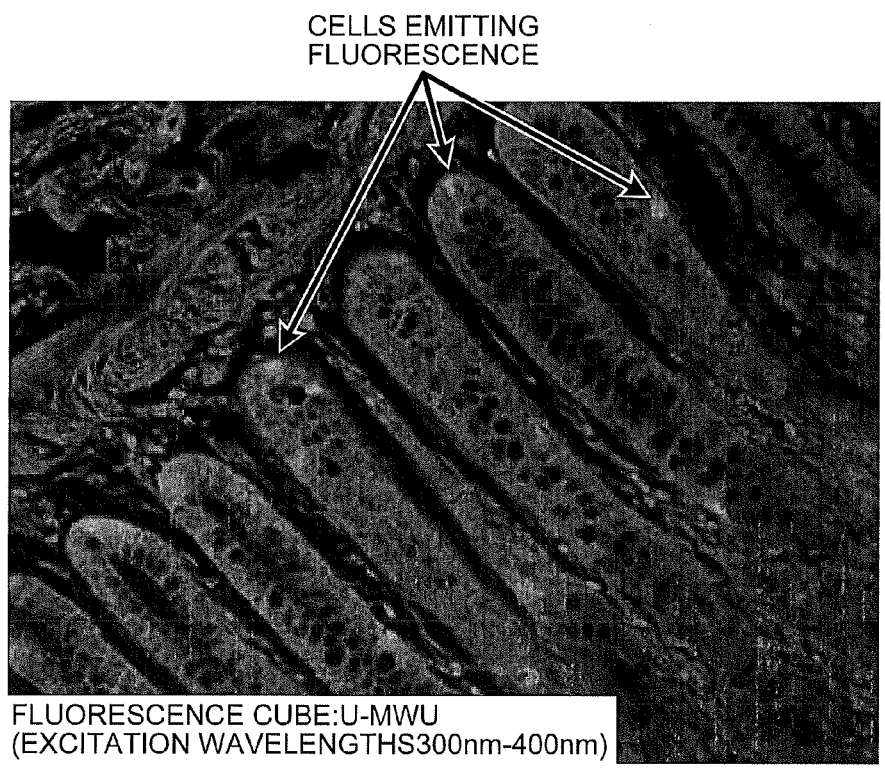
FIG. 6 is a fluorescence observation image (excitation wavelengths of 300 nm to 400 nm, and imaging wavelengths of 400 nm to 700 nm) of an unstained specimen of the mucosa of the large intestine.

FIG. 6 is a fluorescence observation image of when a different unstained specimen of the mucosa of the large intestine from FIG. 3 was observed in a wavelength band of the excitation light (excitation wavelengths) of 300 nm to 400 nm, and imaging wavelengths of 400 nm to 700 nm. A U-MWU cube made by Olympus Corporation was used as a fluorescence cube. In this case, the entire image appeared bluish. Cells emitting green fluorescence were observed in the epithelium M1. When the same unstained specimen as FIG. 6 was observed in a wavelength band of the excitation light of 460 nm to 500 nm and imaging wavelengths of 510 nm to 550 nm, the entire image appeared greenish, and strong fluorescence from the cells emitting fluorescence (see FIG. 6) was observed. Moreover, in a case of a wavelength band of the excitation light of 530 nm to 560 nm and imaging wavelengths of 570 nm to 700 nm, the entire image appeared orangish, and strong fluorescence from the cells emitting fluorescence (see FIG. 6) was observed.

Figure 7:
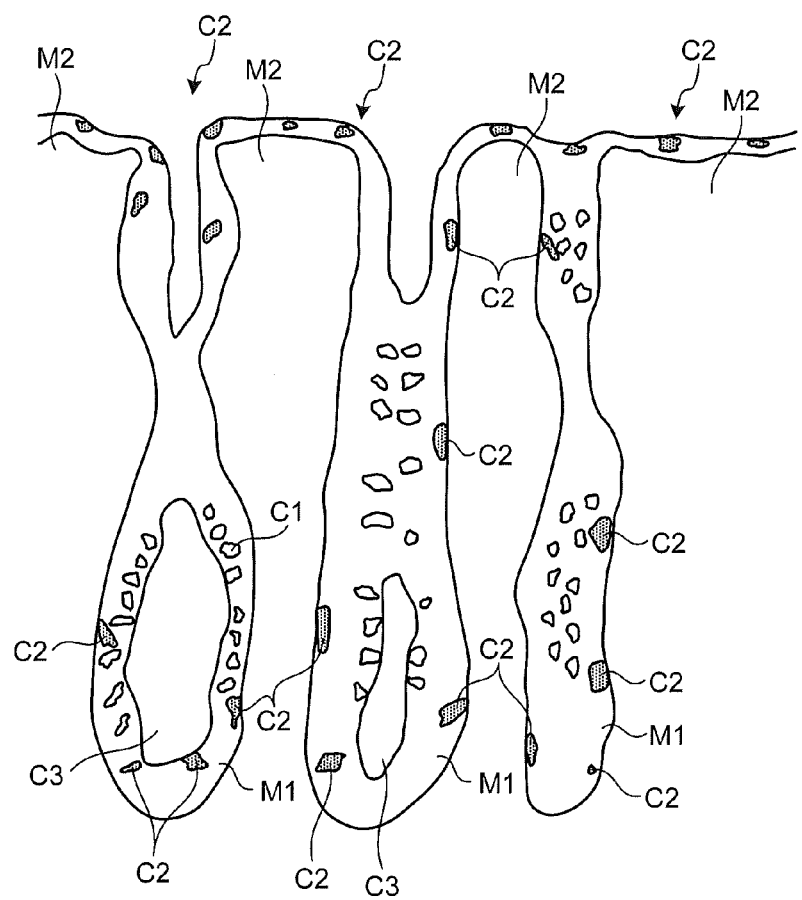
FIG. 7 is a diagram graphically representing a part of a fluorescence observation image of an unstained specimen of the mucosa of the large intestine.

FIG. 7 is a diagram graphically representing a part of a fluorescence observation image of an unstained specimen of the mucosa of the large intestine. As illustrated in FIG. 7, the mucosa of the large intestine includes the epithelium M1 and the lamina propria M2 existing between and below the epithelia M1. Moreover, gland lumens C3 can be seen inside and in the upper part of the epithelium M1. Cells C2 emitting fluorescence, together with goblet cells C1, are observed in the epithelium M1. In FIG. 7, a dot pattern is assigned to the cells C2 emitting fluorescence.

In this manner, the inventor of the present application found that when an unstained specimen of the normal mucosa of the large intestine is irradiated with the excitation light, autofluorescencing cells are observed. Moreover, the inventor of the present application observed multiple fluorescence observation images of unstained specimens of gland ducts in addition to FIG. 3 to FIG. 6 and found that the number of the cells C2 emitting fluorescence changes between normal and abnormal states. Furthermore, the inventor of the present application obtained a finding that the cells C2 emitting fluorescence are endocrine cells as a result of a diligent consideration of the observation results of these fluorescence observation images.

The inventor of the present application has come to make the invention of the present application that detects an area emitting fluorescence based on the fluorescence intensity and the optical spectrum from a fluorescence observation image of an unstained specimen of a gland duct to determine whether or not endocrine cells exist or whether the number of endocrine cells decreases or increases compared with the normal state, and then determines the state of the gland duct based on the determination result.

Figure 8:
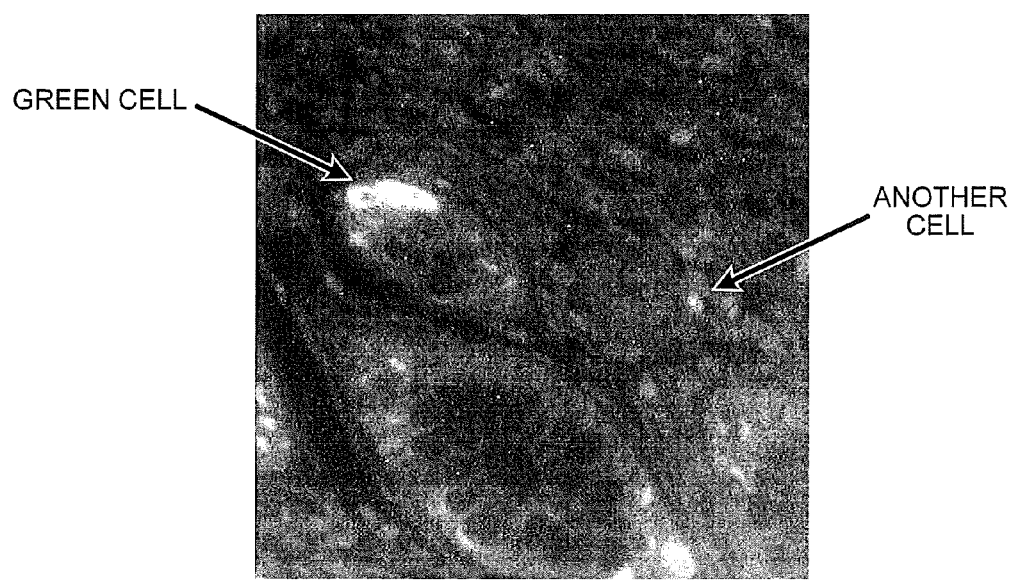
FIG. 8 is a fluorescence observation image of an unstained specimen of the mucosa of the large intestine.
Figure 9:
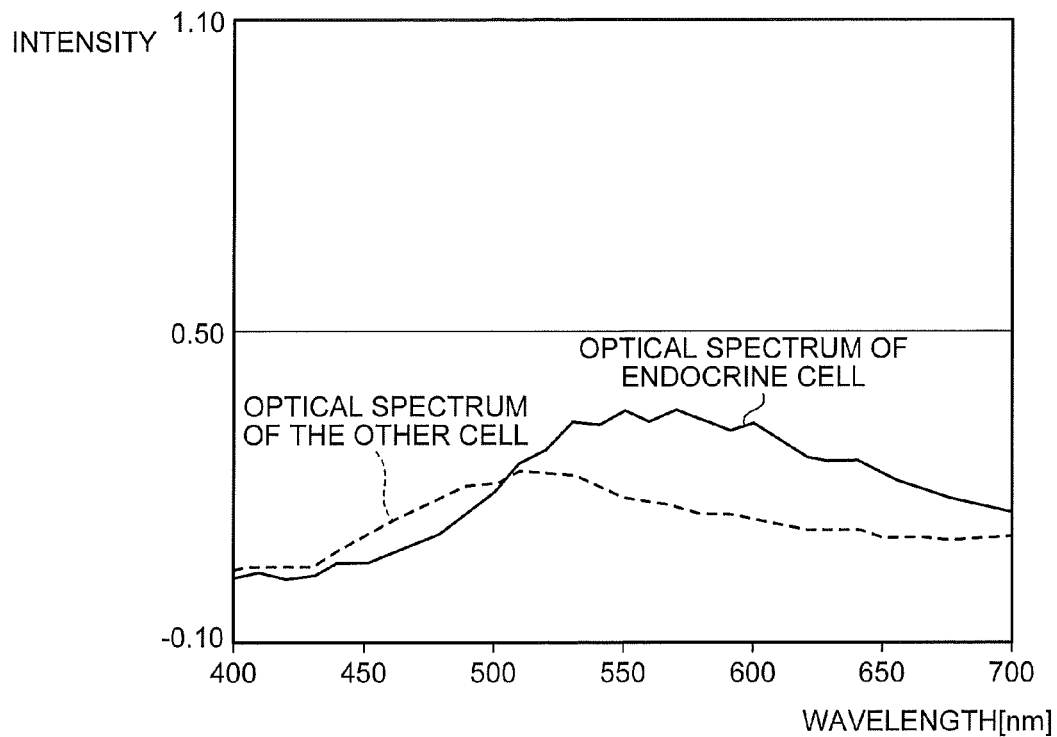
FIG. 9 is a diagram illustrating optical spectra based on the image illustrated in FIG. 8.

FIG. 8 is an image displaying a specimen of the mucosa of the large intestine, in which the condition of the background of a glass slide is changed. FIG. 9 is a diagram illustrating the optical spectra of the image. In FIG. 9, the horizontal axis indicates the wavelength, and the vertical axis indicates the normalized intensity. VariSpec being a liquid crystal tunable filter manufactured by CRI (USA) is used upon image capture.

As illustrated in FIG. 9, the optical spectrum of a cell emitting green fluorescence (hereinafter, the green cell) illustrated in FIG. 8 was observed across wavelengths of 480 nm to 700 nm with the peak around 550 nm. On the other hand, the optical spectrum of another cell is reduced in intensity at wavelengths exceeding 510 nm with the peak around 510 nm. The fluorescence intensity of the green cell is distinctively higher than that of the other cell at wavelengths longer than 510 nm.

In this manner, the fluorescence intensity and the wavelength band of the optical spectrum are different between the cell C2 emitting fluorescence and the other cell in the fluorescence observation image. Accordingly, it is possible to separate the cell C2 emitting fluorescence from the other cell and detects the cell C2 based on the fluorescence intensity and the wavelength of the optical spectrum.

As illustrated in FIG. 1, an image processing apparatus 10 according to the first embodiment includes an input unit 11 that accepts the input of an instruction and information into the image processing apparatus 10, an image acquiring unit 12 that acquires image information (image data) corresponding to a processing target image, an output unit 13 that outputs the processing target image and various calculation results, a recording unit 14, a calculation unit 15 that performs a specified calculation process on an input image, and a control unit 16 that controls the operations of these units. Moreover, the image processing apparatus 10 may be connected to an image display unit 17 that displays, on its screen, the image and calculation results, which are output from the output unit 13, and various other pieces of information.

The input unit 11 includes input devices such as a keyboard, various buttons, and various switches, and pointing devices such as a mouse and a touch panel. Signals corresponding to operations on these devices are input into the control unit 16.

The image acquiring unit 12 is an interface that accepts the input of image data output from an imaging apparatus (camera) attached to, for example, a microscope apparatus, a server, or the like (none of which is illustrated). The image acquiring unit 12 may capture image data directly from the imaging apparatus in real time, or may capture image data temporarily stored in the server at any time.

The recording unit 14 is configured by a semiconductor memory, such as a flash memory, RAM, or ROM, that can perform updating and recording, a recording medium, such as a hard disk, MO, CD-R, or DVD-R, that is built in or connected by a data communication terminal, a reading apparatus that reads information recorded in the recording medium, and the like. The recording unit 14 records the image data captured by the image acquiring unit 12, and various programs and various pieces of setting information to be executed by the calculation unit 15 and the control unit 16. Specifically, the recording unit 14 includes an image processing program recording unit 14a that records an image processing program that uses an image acquired by irradiating an unstained specimen of a gland duct with the excitation light and observing fluorescence emitted from the unstained specimen (hereinafter also referred to as the fluorescence observation image) to determine the abnormality of the gland duct shown in the image.

The calculation unit 15 is configured by hardware, for example, a CPU, and reads various programs recorded in the image processing program recording unit 14a and accordingly executes image processing that determines the abnormality of the gland duct shown in the fluorescence observation image based on the image data of the fluorescence observation image of the gland duct recorded in the recording unit 14.

More specifically, the calculation unit 15 includes a fluorescence intensity computation unit 151 that computes a value corresponding to the intensity of fluorescence emitted from a gland duct being a subject based on the image data acquired by the image acquiring unit 12, and an image determination unit 152 that determines, based on the corresponding value computed by the fluorescence intensity computation unit 151, whether or not the gland duct shown in the fluorescence observation image has an abnormality.

The fluorescence intensity computation unit 151 computes the luminance value of each pixel in the fluorescence observation image, as the value corresponding to the intensity of fluorescence emitting from the gland duct.

The image determination unit 152 compares the luminance value computed for each pixel in the fluorescence observation image, or a representative value or total value of these luminance values with a specified reference value to determine whether or not the gland duct has an abnormality.

The image display unit 17 is configured by a display device, such as, an LCD, EL display, or CRT display, and displays, on the screen, the image and various pieces of information, which are output from the output unit 13 of the image processing apparatus 10.

Next, reference will be made to an image processing method according to the first embodiment of the present invention.

Firstly, an image to be processed by the image processing apparatus of the present invention is, for example, an image captured by the following work. In other words, a pathological specimen of a gland duct extracted from a living body is paraffin embedded, sliced, and fixed on a glass slide. A cover glass is then bonded to the thin section on the glass slide, which is left unstained, using a mounting medium. Accordingly, a prepared slide of the unstained specimen of the gland duct is created.

Next, the unstained specimen of the gland duct is placed on the stage of an epi-illumination microscope to which a CCD camera is attached. Moreover, a fluorescence cube that can irradiate the specimen with the excitation light in a desired wavelength band and transmit observation light (fluorescence) in a desired wavelength band from the specimen is attached to the epi-illumination microscope. The unstained specimen is then irradiated with the excitation light. Fluorescence generated by the irradiation is captured by the CCD camera to generate image data of a fluorescence observation image.

The image acquiring unit 12 acquires the image data generated in this manner, and records the image data in the recording unit 14. It may be configured such that the image data generated by the CCD camera is temporarily recorded in a server or the like, and is acquired by the image acquiring unit 12 from the server, or that the image processing apparatus 10 illustrated in FIG. 1 is connected to the epi-illumination microscope, and the image acquiring unit 12 captures the image data directly from the epi-illumination microscope, and records the image data in the recording unit 14.

Figure 10:
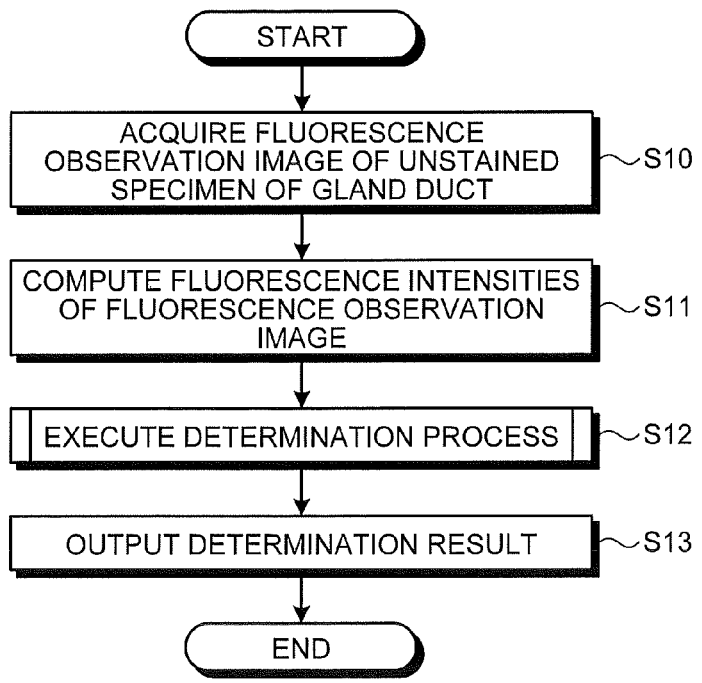
FIG. 10 is a flowchart illustrating the operation of the image processing apparatus illustrated in FIG. 1.

Next, the fluorescence observation image generated in this manner is processed by the image processing apparatus 10. FIG. 10 is a flowchart illustrating the operation of the image processing apparatus 10.

In Step S10, the calculation unit 15 acquires a fluorescence observation image of an unstained specimen of a gland duct by reading image data captured by the image processing apparatus 10 via the image acquiring unit 12 and recorded in the recording unit 14. In the first embodiment, an unstained specimen of the mucosa of the large intestine is assumed to be observed as an example.

In the following Step S11, the fluorescence intensity computation unit 151 computes a value corresponding to the fluorescence intensity at each pixel position in the fluorescence observed image. Specifically, the fluorescence intensity computation unit 151 computes a luminance value from the pixel value of each pixel, and uses the luminance value as the fluorescence intensity. A luminance value Y is given by the following equation (1) in a case where the fluorescence observation image is a color image having specified pixel levels (for example, 256-grayscale) for the wavelength components (color components) of red (R), green (G), and blue (B).

$$Y = 0.30R + 0.59G + 0.11B \quad (1)$$

In Step S12, the image determination unit 152 determines, based on the fluorescence intensities computed from the fluorescence observation image, whether or not the gland duct shown in the fluorescence observation image has an abnormality.

When the observation target gland duct is the mucosa of the stomach, small intestine, large intestine, or prostate gland, there is a characteristic that endocrine cells are observed when the gland duct is normal, and the number of endocrine cells decreases when the gland duct is abnormal. Hence, the image determination unit 152 determines the abnormality of the gland duct from the fluorescence intensities indicating the existence of endocrine cells based on such a characteristic.

Figure 11:
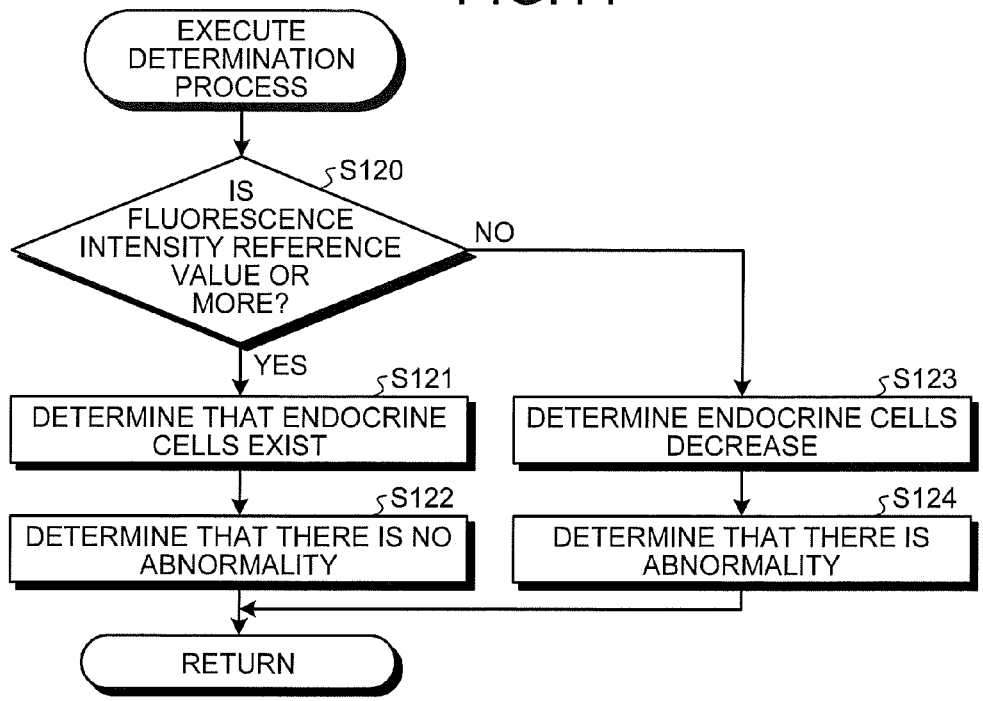
FIG. 11 is a flowchart illustrating the determination process (for a gland duct being the mucosa of the stomach, small intestine, large intestine, or prostate gland) illustrated in FIG. 10.

FIG. 11 is a flowchart illustrating the determination process executed in Step S12. In Step S120, the image determination unit 152 compares the fluorescence intensity computed from the fluorescence observation image with a specified reference value. The fluorescence intensity compared with the reference value may be, for example, a total or average value of the luminance values of the pixels, or a representative value (for example, a maximum value) of the luminance values of the pixels. Moreover, the reference value is required to be set for each organ of an observation target by collecting and analyzing luminance value data on fluorescence observation images of unstained specimens of normal and abnormal gland ducts.

When the fluorescence intensity is the reference value or more (Step S120: Yes), the image determination unit 152 determines that endocrine cells exist in the fluorescence observation image (presence of endocrine cells) (Step S121). In this case, the image determination unit 152 determines that the observation target gland duct has no abnormality (Step S122). The process subsequently returns to the main routine.

On the other hand, when the fluorescence intensity is smaller than the reference value (Step S120: No), the image determination unit 152 determines that endocrine cells do not exist or decrease in number compared with the normal state (decrease in the number of endocrine cells) in the fluorescence observation image (Step S123). In this case, the image determination unit 152 determines that the observation target gland duct has an abnormality (Step S124). The process subsequently returns to the main routine.

In Step S13 subsequent to Step S12, the calculation unit 15 outputs the determination result by the image determination unit 152. In response to this, the control unit 16 records the determination result in the recording unit 14 while causing the output unit 13 to output the determination result and causing the image display unit 17 to display the determination result. Specifically, the control unit 16 causes the image display unit 17 to display the determination result such as "no abnormality detected"/"abnormality detected" in text. Moreover, in addition, the image display unit 17 may be caused to display the fluorescence observation image that is determined. At this time, in the case of "no abnormality detected," an area with high fluorescence intensity, that is, an area of an endocrine cell may be marked and displayed. The operation of the image processing apparatus 10 then terminates.

As described above, according to the first embodiment, the fluorescence intensity of a fluorescence observation image of an unstained specimen of a gland duct such as the mucosa of the large intestine is compared with the reference value, and the presence or absence of an area that emits autofluorescence is determined. Accordingly, it is possible to determine whether or not endocrine cells exist and determine whether or not the gland duct has an abnormality based on the determination result. Therefore, it becomes possible to automatically, easily, and stably make a determination on the unstained specimen of the gland duct without human effort.

First Modification

Next, a first modification of the first embodiment of the present invention is described.

Entire configurations of the image processing apparatus and the image processing method according to the first modification are similar to those of FIG. 1 and FIG. 10, and are different from the first embodiment only in the determination method in Step S12 illustrated in FIG. 10.

Figure 12:
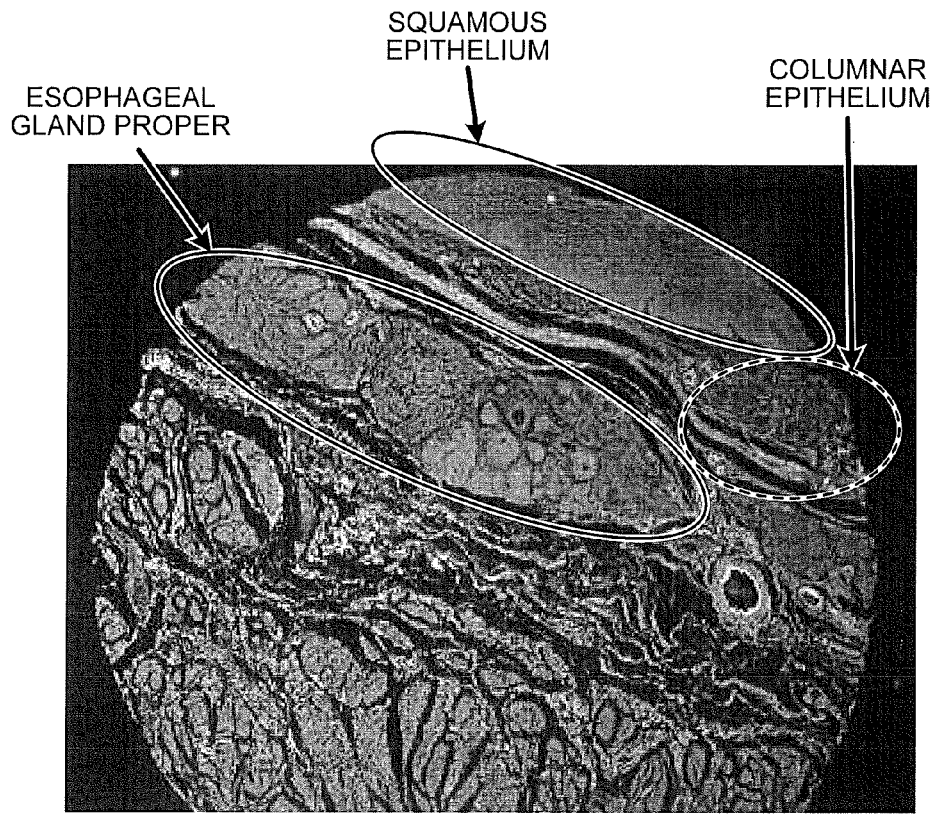
FIG. 12 is a fluorescence observation image (excitation wavelengths of 300 nm to 400 nm, and imaging wavelengths of 400 nm to 700 nm) of an unstained specimen of the mucosa of the esophagus.

When the observation target gland duct is the mucosa of the esophagus, there is a characteristic that endocrine cells do not exist when the gland duct is normal, and endocrine cells are observed when the gland duct becomes abnormal. FIG. 12 is a fluorescence observation image of when an unstained specimen of the mucosa of the esophagus was observed in a wavelength band of the excitation light of 300 nm to 400 nm, and imaging wavelengths of 400 nm to 700 nm. When the mucosa of the esophagus is normal, the esophageal epithelium is composed of a squamous epithelium. On the other hand, the squamous epithelium that is weak against the gastric juice of the stomach and is replaced by a columnar epithelium (see FIG. 12) existing in the stomach due to the reflux of the gastric juice into the esophagus is called Barrett's mucosa, and the esophagus having Barrett's mucosa is called Barrett's esophagus (reference: Edited by Masamune Shimo, "Seijo gazo to kurabete wakaru byouri Atlas (Pathological Atlas Understandable by Comparison with Normal Images)," Yodosya Co., Ltd, p. 16). Barrett's esophagus is known to progress to Barrett's esophageal cancer. Canceration can be prevented by stopping the progress with early detection and treatment. Especially, it is difficult to be aware of esophageal cancer in the early stage of the development. Accordingly, a technique capable of finding it early is desired.

Figure 13:
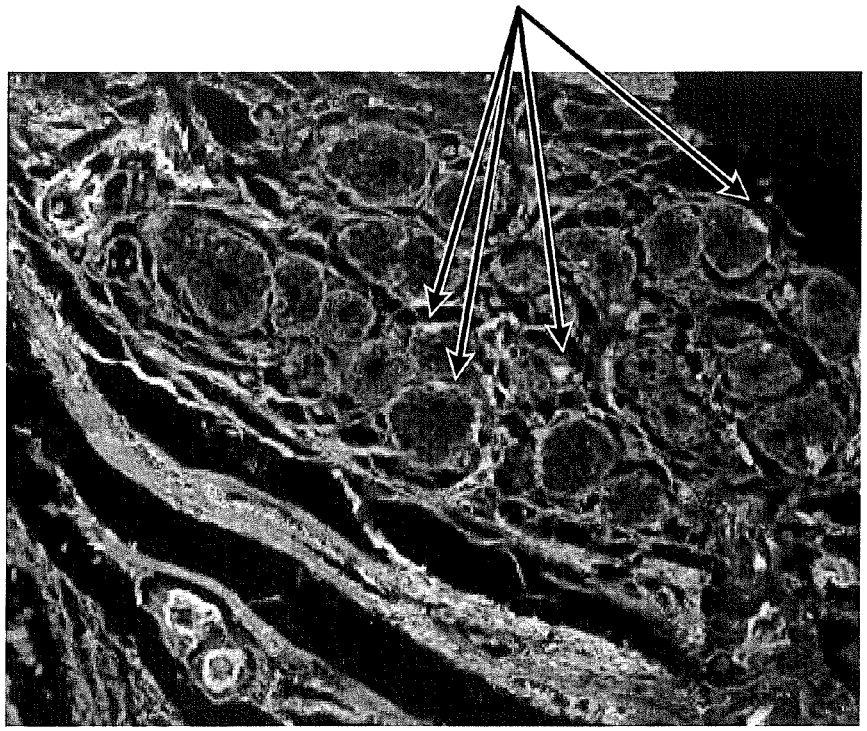
FIG. 13 is an enlarged image of the columnar epithelium portion illustrated in FIG. 12.

FIG. 13 is an enlarged image of the columnar epithelium portion illustrated in FIG. 12. As illustrated in FIG. 13, autofluorescencing areas indicating existence of endocrine cells were observed in the fluorescence observation image showing the columnar epithelium (that is, Barrett's mucosa).

Hence, in the first modification, reference will be made to a case where the observation target gland duct is the mucosa of the esophagus.

Figure 14:
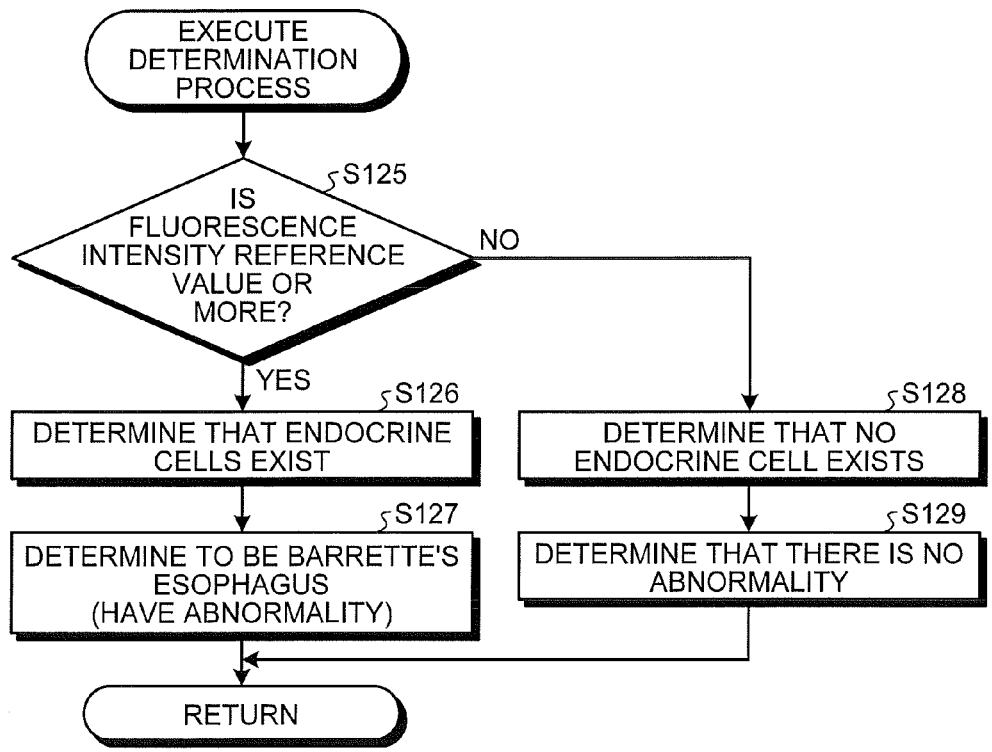
FIG. 14 is a flowchart illustrating the determination process (for a gland duct being the mucosa of the esophagus) illustrated in FIG. 10.

FIG. 14 is a flowchart illustrating the determination process executed in Step S12. In Step S125, the image determination unit 152 compares the fluorescence intensity computed from the fluorescence observation image with a specified reference value. The fluorescence intensity compared with the reference value may be a total or average value of the luminance values of the pixels, or a representative value (such as, a maximum value) of the luminance values of the pixels as in the first embodiment. Moreover, the reference value is required to be set by collecting and analyzing luminance value data on fluorescence observation images of unstained specimens of normal and abnormal mucosae of the esophagus.

When the fluorescence intensity is the reference value or more (Step S125: Yes), the image determination unit 152 determines that endocrine cells exist in the fluorescence observation image (presence of endocrine cells) (Step S126). In this case, the observation target gland duct (the mucosa of the esophagus) turns into Barrett's esophagus, and the image determination unit 152 determines that the gland duct has an abnormality (Step S127). The process subsequently returns to the main routine.

On the other hand, when the fluorescence intensity is smaller than the reference value (Step S125: No), the image determination unit 152 determines that endocrine cells do not exist (absence of endocrine cells) in the fluorescence observation image (Step S128). In this case, the image determination unit 152 determines that the mucosa of the esophagus of the observation target has no abnormality (Step S129). The process subsequently returns to the main routine.

In Step S13 subsequent to Step S12 (see FIG. 10), the calculation unit 15 outputs the determination result by the image determination unit 152. In response to this, the control unit 16 causes the output unit 13 to output the determination result and causes the image display unit 17 to display the determination result. At this time, it may be configured such that the control unit 16 causes the image display unit 17 to display the determination result of "no abnormality detected"/"abnormality detected" in text and to display the fluorescence observation image that is determined. In a case of "no abnormality detected," an area with high fluorescence intensity, that is, an area of Barrett's mucosa where the endocrine cells are observed may be marked and displayed.

As described above, according to the first modification of the first embodiment, the fluorescence intensity of a fluorescence observation image of an unstained specimen of the mucosa of the esophagus is compared with the reference value, and the presence or absence of areas that emit autofluorescence is determined. Accordingly, it is possible to determine whether or not endocrine cells exist and then determine whether or not the mucosa of the esophagus turns into Barrett's mucosa based on the determination result. Therefore, it becomes possible to automatically, easily, and stably make a determination on the unstained specimen of the mucosa of the esophagus without human effort.

Second Embodiment

Next, a second embodiment of the present invention is described.

Figure 15:
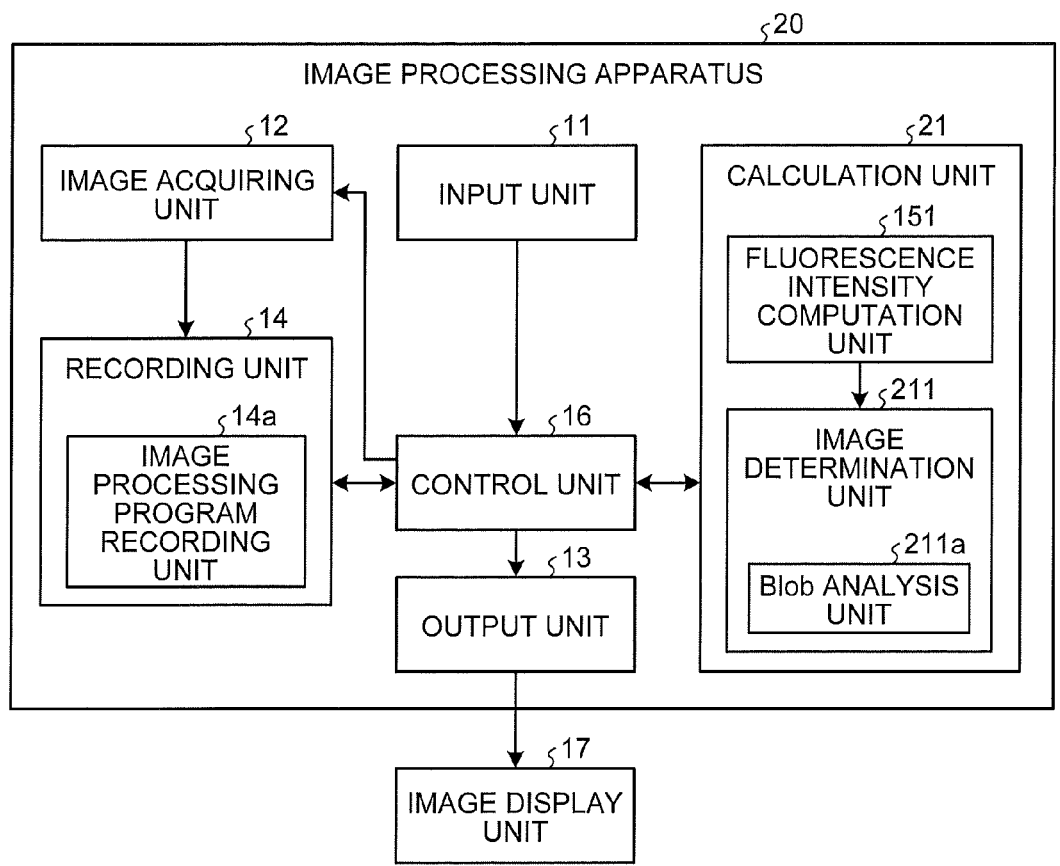
FIG. 15 is a block diagram illustrating the configuration of an image processing apparatus according to a second embodiment of the present invention.

FIG. 15 is a block diagram illustrating the configuration of an image processing apparatus according to the second embodiment of the present invention. As illustrated in FIG. 15, an image processing apparatus 20 according to the second embodiment includes a calculation unit 21 having an image determination unit 211, instead of the image determination unit 152 illustrated in FIG. 1. The configurations and operations of the units of the image processing apparatus 20, other than the image determination unit 211, are similar to those of the first embodiment.

The image determination unit 211 includes a blob analysis unit 211a that performs blob analysis based on the fluorescence intensities (luminance values) computed by the fluorescence intensity computation unit 151. Blob analysis is image processing that treats either of two values (white and black) as a lump (blob) in a binary image obtained by binarizing a processing target image, and analyzing the blob shape features such as the presence or absence, number, area, length, perimeter, and roundness.

The blob analysis unit 211a extracts pixel areas in which the fluorescence intensity is a reference value or more (areas representing cells emitting autofluorescence, and hereinafter also referred to as fluorescence areas) from the pixels of the fluorescence observation image, analyzes the extracted fluorescence areas, and computes characteristic amounts representing the features of the fluorescence areas such as the presence or absence, number, area, length, perimeter, and roundness. The image determination unit 211 determines the abnormality of the gland duct shown in the fluorescence observation image based on the analysis result (that is, the characteristic amounts of the fluorescence areas) of the blob analysis unit 211a.

Figure 16:
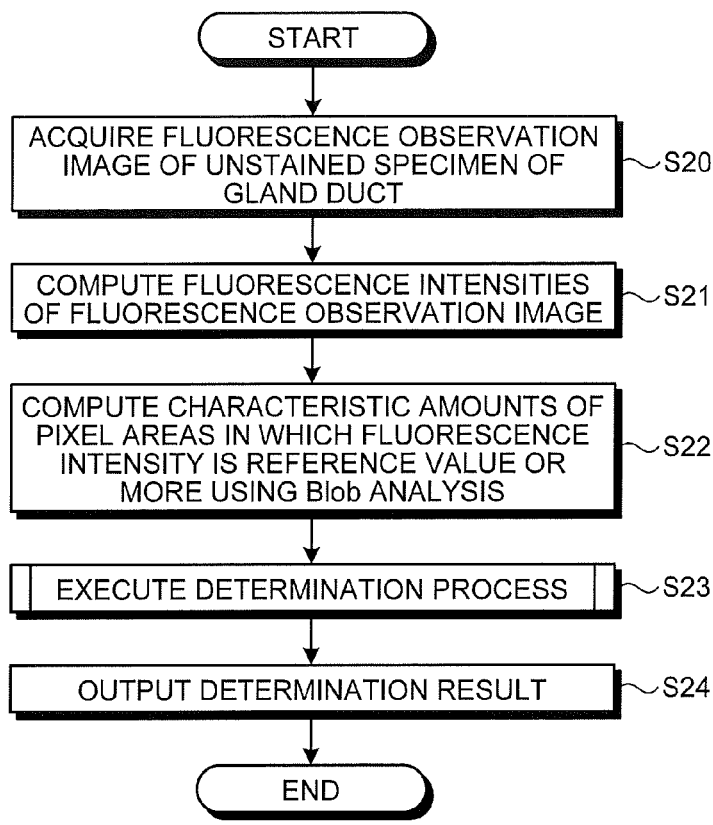
FIG. 16 is a flowchart illustrating the operation of the image processing apparatus illustrated in FIG. 15.

Next, reference will be made to an image processing method according to the second embodiment. FIG. 16 is a flowchart illustrating the operation of the image processing apparatus 20. The process is similar to that of the first embodiment until creating an unstained specimen of a gland duct and generating a fluorescence observation image. Moreover, Steps S20 and S21 illustrated in FIG. 16 correspond to Steps S10 and S11 illustrated in FIG. 10.

In Step S22 subsequent to Step S21, the blob analysis unit 211a computes the characteristic amounts of the pixel areas in which the fluorescence intensity is a reference value or more using blob analysis for the fluorescence observation image. More specifically, the blob analysis unit 211a provides a pixel value, one, to pixels whose luminance value is the reference value or more, and a pixel value, zero, to the other pixels, among the pixels in the fluorescence observation image, and creates a binary image.

The reference value used in the binarization process is required to be obtained, for example, from the distribution of luminance value data collected in advance from fluorescence observation images of unstained specimens of normal and abnormal gland ducts, by a well-known method such as the discriminant analysis, percentile method, or mode method (reference: "Digital gazo syori (Digital Image Processing)", Computer Graphic Arts Society, pp. 174-176).

Furthermore, the blob analysis unit 211a computes characteristic amounts illustrated below for areas (fluorescence areas) of pixels having the pixel value one in the binary image.

(1) The representative value (average, mode, or the like) or total value of the area (number of pixels) of each fluorescence area.

(2) The number of fluorescence areas whose area is a specified threshold value (area threshold value) or more.

(3) The ratio of a total value of the areas of the fluorescence areas whose area is the specified threshold value (area threshold value) or more to the area of the entire fluorescence observation image.

(4) The number of fluorescence areas whose perimeter is a specified threshold value or more (perimeter threshold value).

(5) The number of fluorescence areas whose circumscribed distance is a specified threshold value or more (circumscribed distance threshold value).

(6) The representative value (average, mode, or the like) value of roundness of the fluorescence areas.

(7) The luminance values of respective areas in the fluorescence observation image corresponding to the fluorescence areas extracted from the binary image, or the total value of these luminance values.

The above characteristic amount may be obtained by extracting the pixels having the pixel value one from the binary image, then performing a general labeling process, and computing shape feature parameters, instead of performing blob analysis (reference: "Digital gazo syori (Digital Image Processing)", Computer Graphic Arts Society, pp. 181-184).

In the following Step S23, the image determination unit 211 determines whether or not the gland duct shown in the fluorescence observation image is abnormal, based on the characteristic amounts computed in Step S22. As described above, when the observation target gland duct is the mucosa of the stomach, small intestine, large intestine, or prostate gland, there is the characteristic that endocrine cells are observed when the gland duct is normal, and the number of endocrine cells decreases when the gland duct is abnormal. Accordingly, the image determination unit 211 determines the abnormality of the gland duct from the characteristic amount indicating the existence of endocrine cells based on such a characteristic.

Figure 17:
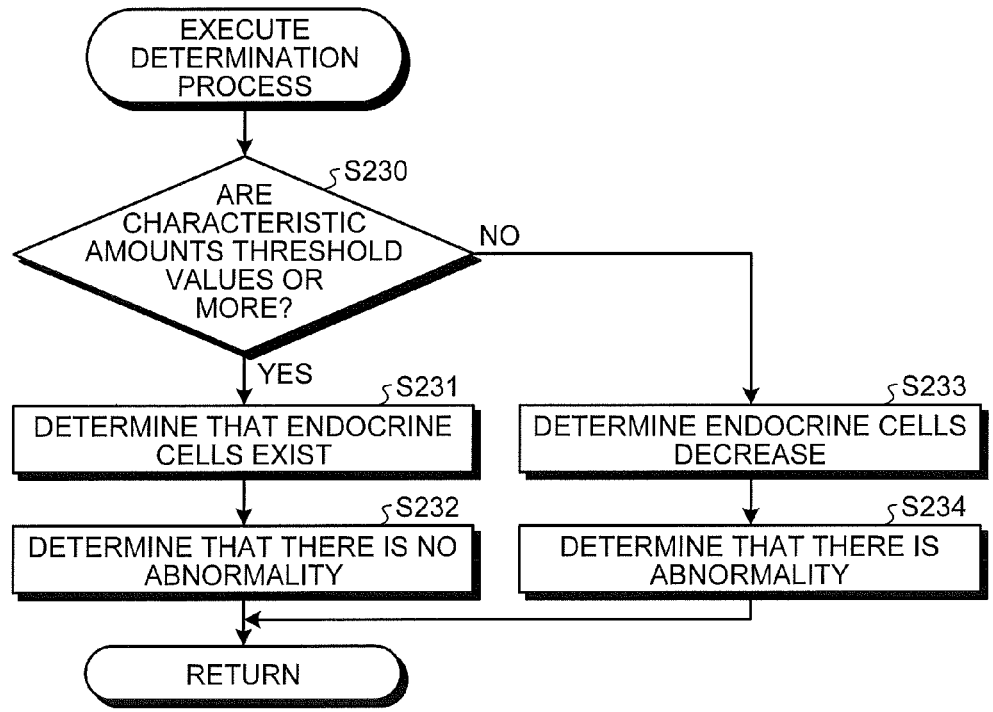
FIG. 17 is a flowchart illustrating the determination process (for a gland duct being the mucosa of the stomach, small intestine, large intestine, or prostate gland) illustrated in FIG. 16.

FIG. 17 is a flowchart illustrating the determination process executed in Step S23. In Step S230, the image determination unit 211 compares the characteristic amounts computed in Step S22 with specified threshold values. The threshold values compared with the characteristic amounts are set according to the kinds of the characteristic amounts (1) to (7), based on the previously acquired luminance value data of the fluorescence observation images of unstained specimens of the normal and abnormal mucosae of the stomach, small intestine, large intestine, or prostate gland. The threshold values may be set according to the each organ.

When the characteristic amounts are the threshold values or more (Step S230: Yes), in other words, when the number of fluorescence areas is large, the area of fluorescence areas is larger than a specified case, the luminance of fluorescence areas is higher than a specified case, and the shapes of fluorescence areas are close to a circle, the image determination unit 211 determines that endocrine cells exist (presence of endocrine cells) in the fluorescence observation image (Step S231). In this case, the image determination unit 211 determines that the observation target gland duct has no abnormality (Step S232). The process subsequently returns to the main routine.

On the other hand, when the characteristic amounts are less than the threshold values (Step S230: No), in other words, when the number of fluorescence areas is small, the area of fluorescence areas is smaller than the specified case, the luminance of fluorescence areas is lower than the specified case, and the shapes of fluorescence areas are different from a circle, the image determination unit 211 determines that endocrine cells do not exist or decrease in number than the normal state (decrease in the number of endocrine cells) in the fluorescence observation image (Step S233). In this case, the image determination unit 211 determines the observation target gland duct has an abnormality (Step S234). The process subsequently returns to the main routine.

In Step S24 subsequent to Step S23, the calculation unit 21 outputs the determination result by the image determination unit 211. In response to this, the control unit 16 records the determination result in the recording unit 14 while causing the output unit 13 to output the determination result and causing the image display unit 17 to display the determination result. Specifically, the control unit 16 causes the image display unit 17 to display the determination result such as "no abnormality detected"/"abnormality detected" in text. Moreover, in addition, the image display unit 17 may be caused to display the fluorescence observation image that is determined. At this time, in the case of "no abnormality detected," an area with the large amount of characteristic amount, that is, an area of an endocrine cell may be marked and displayed. The operation of the image processing apparatus 20 then terminates.

As described above, according to the second embodiment, whether or not endocrine cells exist in a gland duct is determined based on the characteristic amounts computed for the fluorescence areas extracted from a fluorescence observation image of an unstained specimen of the gland duct, and whether or not the gland duct is abnormal is determined based on the determination result. Accordingly, the accuracy of determination on the gland duct can be improved. Therefore, it becomes possible to make a determination on the unstained specimen of the gland duct more accurately.

Second Modification

Next, a second modification of the second embodiment of the present invention is described.

Entire configurations of the image processing apparatus and the image processing method according to the second modification are similar to those of FIG. 15 and FIG. 16, and are different from the second embodiment only in the determination method in Step S23 illustrated in FIG. 16.

When the observation target gland duct is the mucosa of the esophagus, endocrine cells do not exist when the gland duct is normal, and endocrine cells are observed when the gland duct becomes abnormal, as described above. In the second modification, reference will be made to a case where the observation target gland duct is the mucosa of the esophagus.

Figure 18:
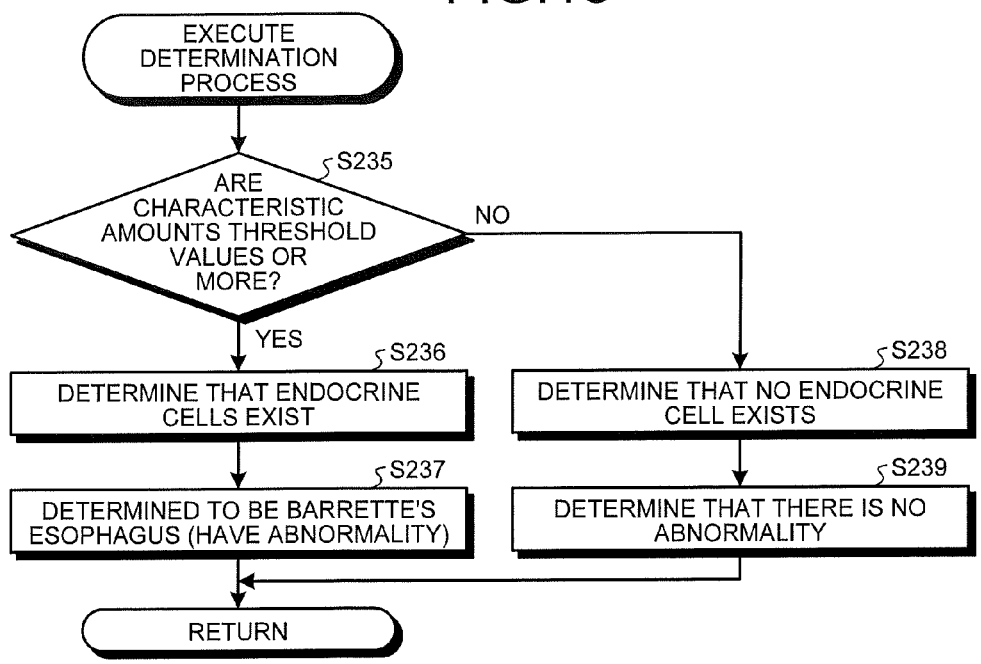
FIG. 18 is a flowchart illustrating the determination process (for a gland duct being the mucosa of the esophagus) illustrated in FIG. 16.

FIG. 18 is a flowchart illustrating the determination process executed in Step S23. In Step S235, the image determination unit 211 compares the characteristic amounts computed in Step S22 with specified threshold values. The threshold values compared with the characteristic amounts are set according to the kinds of the characteristic amounts (1) to (7), based on the previously acquired luminance value data of fluorescence observation images of unstained specimens of the normal and abnormal mucosae of the esophagus.

When the characteristic amounts are the threshold values or more (Step S235: Yes), the image determination unit 211 determines that endocrine cells exist (presence of endocrine cells) in the fluorescence observation image (Step S236). In this case, the observation target gland duct (the mucosa of the esophagus) turns into Barrett's esophagus, and the image determination unit 211 determines that the gland duct has an abnormality (Step S237). The process subsequently returns to the main routine.

On the other hand, when the characteristic amounts are smaller than the threshold values (Step S235: No), the image determination unit 211 determines that endocrine cells do not exist (absence of endocrine cells) in the fluorescence observation image (Step S238). In this case, the image determination unit 211 determines the mucosa of the esophagus of the observation target has no abnormality (Step S239). The process subsequently returns to the main routine.

In Step S24 subsequent to Step S23 (see FIG. 16), the calculation unit 21 outputs the determination result by the image determination unit 211. In response to this, the control unit 16 causes the output unit 13 to output the determination result and causes the image display unit 17 to display the determination result. At this time, it may be configured such that the control unit 16 causes the image display unit 17 to display the determination result of "no abnormality detected"/"abnormality detected" in text and, in the case of "abnormality detected," to mark and display the area having large characteristic amounts, in other words, the area of Barrett's mucosa in which endocrine cells are observed.

As described above, according to the second modification of the second embodiment, whether or not endocrine cells exist in the mucosa of the esophagus is determined based on the characteristic amounts computed for the fluorescence areas extracted from a fluorescence observation image of an unstained specimen of the mucosa of the esophagus, and whether or not the mucosa of the esophagus turns into Barrett's mucosa is determined based on the determination result. Accordingly, the accuracy of determination on the mucosa of the esophagus can be improved. Therefore, it becomes possible to make a determination on the unstained specimen of the mucosa of the esophagus automatically and more accurately.

Third Embodiment

Next, a third embodiment of the present invention is described.

Figure 19:
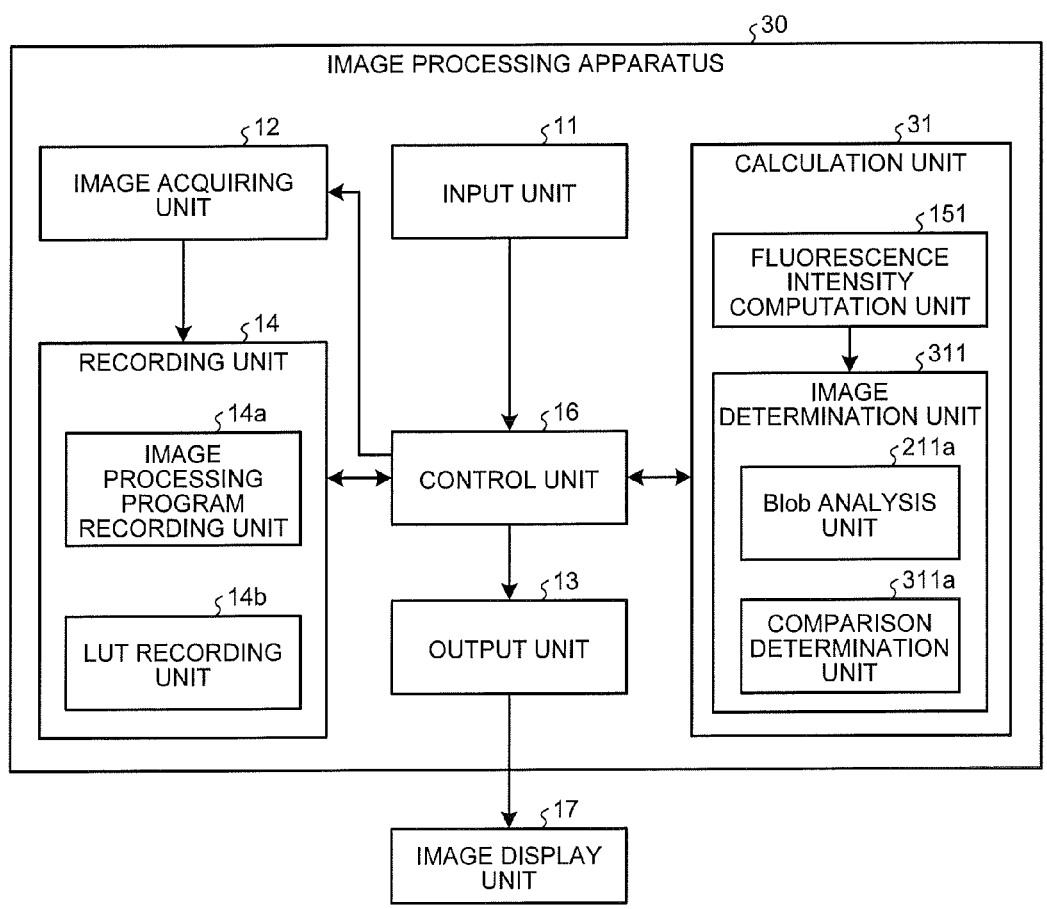
FIG. 19 is a block diagram illustrating the configuration of an image processing apparatus according to a third embodiment of the present invention.

FIG. 19 is a block diagram illustrating the configuration of an image processing apparatus according to the third embodiment of the present invention. As illustrated in FIG. 19, an image processing apparatus 30 according to the third embodiment includes a calculation unit 31 having an image determination unit 311, instead of the image determination unit 211 illustrated in FIG. 15. Moreover, the recording unit 14 includes a lookup table (LUT) recording unit 14b that records lookup tables used upon determination of the image determination unit 311. The configurations and operations of the units of the image processing apparatus 30, other than the image determination unit 311, are similar to those of the second embodiment.

The image determination unit 311 further includes a comparison determination unit 311a in addition to the blob analysis unit 211a. The comparison determination unit 311a refers to the lookup tables recorded in the LUT recording unit 14b to determine the state of a gland duct such as the degree of abnormality of the gland duct, stage of cancer, depth of cancer invasion, and degree of cancer metastasis in accordance with the characteristic amount of the fluorescence areas computed by the blob analysis unit 211a.

Next, reference will be made to the contents of the lookup tables recorded in the LUT recording unit 14b. The lookup tables are information (comparative tables) in which the characteristic amounts of the fluorescence areas computed by the blob analysis unit 211a are associated with the degree of abnormality of the gland duct, stage of cancer, depth of cancer invasion, and degree of cancer metastasis.

Figure 20:
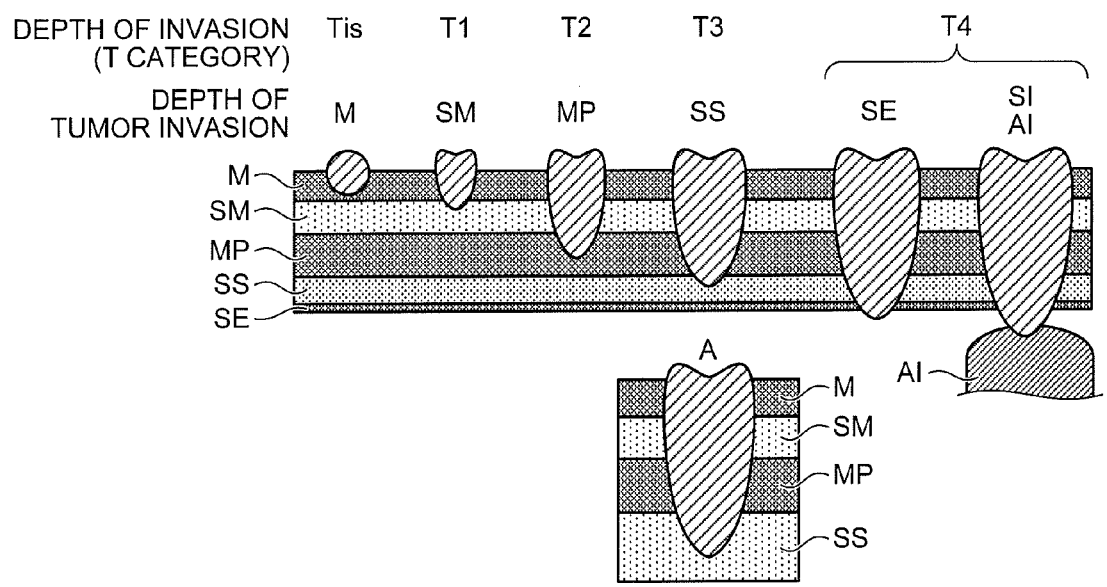
FIG. 20 is a schematic diagram illustrating depth of cancer invasion.

FIG. 20 is a schematic diagram illustrating the level of invasion of cancer in the mucosa of the large intestine as an example of a gland duct. Colorectal cancer is generally known to develop in the mucosa M (the epithelium M1, the lamina propria M2, and the muscularis mucosae M3: see FIG. 2) and invade to the submucosa SM, the muscularis propria MP, the subserosa SS, the serosa SE, and an adjacent organ AI. These degrees of invasion are expressed as the depth of tumor invasion M to SI (AI). Moreover, when cancer invades beyond the muscularis propria MP but does not invade to the adjacent organ AI in a portion having no serosa SE (in other words, a portion that is not covered by the peritoneum), the depth of tumor invasion is A.

Moreover, the TNM classification is known as an indicator indicating the stage of a malignant tumor (cancer) (reference: Edited by Takashi Yao and Takahiro Fujimori, "Syuyo byori kanbetsu shindan Atlas (Atlas of Tumor Pathological Identification Diagnosis) "Daichogan (Colorectal Cancer)," Bunkodo Co., Ltd, pp. 2-10). In the TNM classification, the stage of cancer is expressed by three factors of tumor (T): the depth of invasion of the primary tumor, nodes (N): the presence or otherwise of metastasis to lymph nodes, and metastasis (M): the presence or otherwise of distant metastasis.

In the TNM classification, the depth of cancer invasion is classified into five levels of Tis, T1, T2, T3, and T4 according to the above-mentioned level of invasion. This is called the T category. Specifically, as illustrated in FIG. 20, when the cancer stays in the mucosa M, the depth of invasion is classified as Tis. When the cancer invades to the submucosa SM, the depth of invasion is classified as T1. When the cancer invades to the muscularis propria MP, the depth of invasion is classified as T2. When the cancer invades beyond the muscularis propria MP but is not exposed to the surface of the serosa SE, the depth of invasion is classified as T3. When the cancer is exposed to the surface of the serosa SE, and invades to the adjacent organ AI, the depth of invasion is classified as T4.

The inventor of the present application found that an area that emits autofluorescence in a fluorescence observation image of an unstained specimen of a gland duct, that is, an area of an endocrine cell changes depending of the state of the gland duct such as the above-mentioned stage of cancer. Hence, the inventor of the present application conceived the configuration of the third embodiment that computes the characteristic amounts of a fluorescence area from previously collected fluorescence observation images of unstained specimens of a gland duct, previously associates the characteristic amount with the state of the gland duct, and determines the state of the gland duct based on characteristic amount of a fluorescence area computed from a processing target fluorescence observation image.

FIG. 21A to FIG. 21G are lookup tables applicable to an organ having the characteristic that endocrine cells are observed when a gland duct is normal, and the number of endocrine cells decreases when the gland duct is abnormal, as in the stomach, small intestine, large intestine, or prostate gland. Hereinafter, the contents of the lookup tables are described.

FIG. 21A is an example of a lookup table in which the area (number of pixels) of a fluorescence area is associated with the degree of abnormality of the mucosa of the large intestine (an area-abnormality degree comparative table). In the lookup table, the degree of abnormality is classified into five levels of one to five. Associations are established such that as the area of a fluorescence area becomes smaller, the degree of abnormality becomes higher. The value of an area in each level is an example.

FIG. 21B is an example of a lookup table in which the area (number of pixels) of a fluorescence area is associated with the stage of cancer (an area-stage comparative table). As described above, the stage of cancer is classified into five levels of stages (Stage) 0, I, II, III, and IV in the TNM classification. In the lookup table illustrated in FIG. 21B, associations are established such that as the area of a fluorescence area becomes smaller, the stage advances. The value of an area in each level is an example.

FIG. 21C is an example of a lookup table in which the area (number of pixels) of a fluorescence area is associated with the depth of cancer invasion (T category) (an area-invasion depth (T category) comparative table). As described above, the depth of cancer invasion (T category) is classified into five levels of Tis, T1, T2, T3, and T4 according to the level of invasion in the TNM classification. In the lookup table illustrated in FIG. 21C, associations are established such that as the area of a fluorescence area becomes smaller, the depth of invasion advances. The value of an area in each level is an example.

FIG. 21D is an example of a lookup table in which the area (number of pixels) of a fluorescence area is associated with the degree of cancer metastasis (an area-degree of metastasis comparative table). In the lookup table, the degree of cancer metastasis is indicated by five levels of one to five. Associations are established such that as the area of a fluorescence area becomes smaller, the degree of metastasis becomes higher. The value of an area in each category is an example.

FIG. 21E is an example of a lookup table in which the area (number of pixels) of a fluorescence area is associated with the degree of cancer metastasis (lymph nodes/N category) (an area-degree of metastasis (lymph nodes/N category) comparative table). In the N category, the degree of cancer metastasis is classified as N0: No lymph node metastases detected, N1: N1=One to three lymph node metastases, and N2: Four or more lymph node metastases. In the lookup table illustrated in FIG. 21E, associations are established such that as the area of a fluorescence area becomes smaller, the degree of metastasis becomes higher. The value of an area in each level is an example.

FIG. 21F is an example of a lookup table in which the area (number of pixels) of a fluorescence area is associated with the degree of cancer metastasis (distant metastasis/M category) (an area-degree of metastasis (distant metastasis/M category) comparative table). In the M category, the degree of cancer metastasis is classified as M0: No distant metastasis, and M1: Distant metastasis is present. In the lookup table illustrated in FIG. 21F, associations are established such that as the area of a fluorescence area becomes smaller, the degree of metastasis becomes higher. The value of an area in each level is an example.

FIG. 21G is an example of a lookup table in which the roundness of a fluorescence area is associated with the degree of abnormality of the mucosa of the large intestine (a roundness-abnormality degree comparative table). In the lookup table, the degree of abnormality is classified into five levels of one to five. Associations are established such that as the roundness becomes lower, the degree of abnormality becomes higher. In terms of the roundness, as the value approaches one, the shape approaches a perfect circle. Moreover, the numerical value of roundness in each level is an example.

In FIG. 21A to FIG. 21G, other characteristic amounts computed by the blob analysis unit 211a, that is, the characteristic amounts (1) to (7) described in the second embodiment, instead of the area and roundness of a fluorescence area, may be associated with the indicators. Alternatively, the fluorescence intensity of a fluorescence observation image (the representative value or total value of the pixel values of the pixels) computed by the fluorescence intensity computation unit 151 may be associated with the respective indicators. Upon using any characteristic amount, associations are established in such a manner as to have a tendency that as fluorescence areas decrease in the area, number, and luminance value, the degree of abnormality becomes higher and the cancer progresses.

Figures 22, 23:
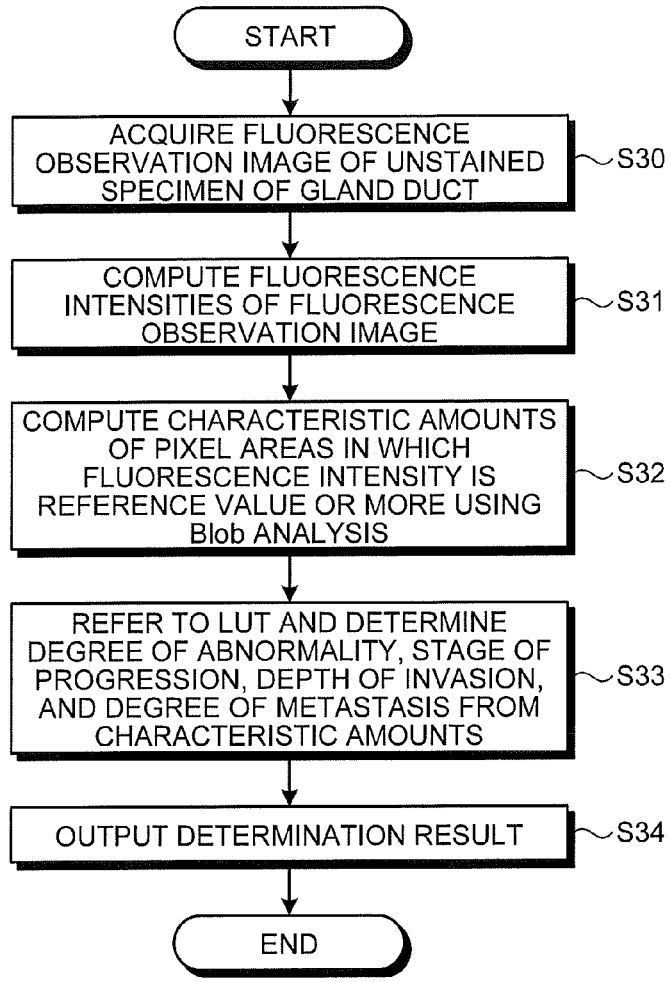
FIG. 22 is a flowchart illustrating the operation of the image processing apparatus illustrated in FIG. 19.
FIG. 23 is a lookup table in which the area (number of pixels) of a fluorescence area is associated with the degree of abnormality of the mucosa of the esophagus.

Next, reference will be made to an image processing method according to the third embodiment. FIG. 22 is a flowchart illustrating the operation of the image processing apparatus 30. The process is similar to that of the first embodiment until creating an unstained specimen of a gland duct and generating a fluorescence observation image. Moreover, Steps S30 to S32 illustrated in FIG. 22 correspond to Steps S20 to S22 illustrated in FIG. 16.

In Step S33 subsequent to Step S32, the comparison determination unit 311a refers to the lookup tables (for example, FIG. 21A to FIG. 21G) recorded in the LUT recording unit 14b to determine the state of the gland duct, in other words, the degree of abnormality, stage of cancer, depth of cancer invasion, and degree of cancer metastasis, based on the characteristic amounts computed by the blob analysis unit 211a. Alternatively, the comparison determination unit 311a may compute the representative value such as an average or mode, or total value from the fluorescence intensities of the pixels computed by the fluorescence intensity computation unit 151, and determine the state of the gland duct based on the representative value or total value.

In the following Step S34, the image determination unit 311 outputs the determination result by the comparison determination unit 311a. In response to this, the control unit 16 records the determination result in the recording unit 14 while causing the image display unit 17 to display the determination result. Specifically, the control unit 16 causes the image display unit 17 to display, on the screen, information such as levels of the degree of abnormality of the gland duct, stage of cancer, depth of cancer invasion, and degree of cancer metastasis. Moreover, a processing target fluorescence observation image may also be displayed on the screen to mark and display a fluorescence area (an area of an endocrine cell).

As described above, according to the third embodiment, it is possible to accurately determine the state of a gland duct, such as the degree of abnormality, stage of cancer, depth of cancer invasion, and degree of cancer metastasis, by referring to information in which characteristic amounts of a fluorescence area in a fluorescence observation image are previously associated with indicators indicating the state of a lesion. Therefore, it becomes possible to make a determination on an unstained specimen of a gland duct automatically and accurately.

Third Modification

Next, a third modification of the third embodiment of the present invention is described.

As described above, when the observation target gland duct is the mucosa of the esophagus, endocrine cells do not exist when the gland duct is normal, and endocrine cells are observed when the gland duct becomes abnormal. Hence, in a case of the mucosa of the esophagus, associations are established in such a manner as to have a tendency that as fluorescence areas increases in the area, number, and luminance value, the degree of abnormality becomes higher and the cancer progresses, unlike the mucosa of the large intestine or the like, in the lookup tables used in Steps S33 of FIG. 22.

FIG. 23 is an example of a lookup table in which the area (number of pixels) of a fluorescence area is associated with the degree of abnormality of the mucosa of the esophagus. In the lookup table, the degree of abnormality is classified into five levels of one to five. Associations are established such that as the area of a fluorescence area becomes larger, the degree of abnormality becomes higher. The value of an area in each level is an example.

As described above, according to the third modification, it is possible to accurately determine the state of the mucosa of the esophagus, such as the degree of abnormality, by referring to information in which the characteristic amount of a fluorescence area in a fluorescence observation image is previously associated with an indicator indicating the state of a lesion. Therefore, it becomes possible to make a determination on an unstained specimen of the mucosa of the esophagus automatically and accurately.

Fourth Embodiment

Next, a fourth embodiment of the present invention is described.

Figure 24:
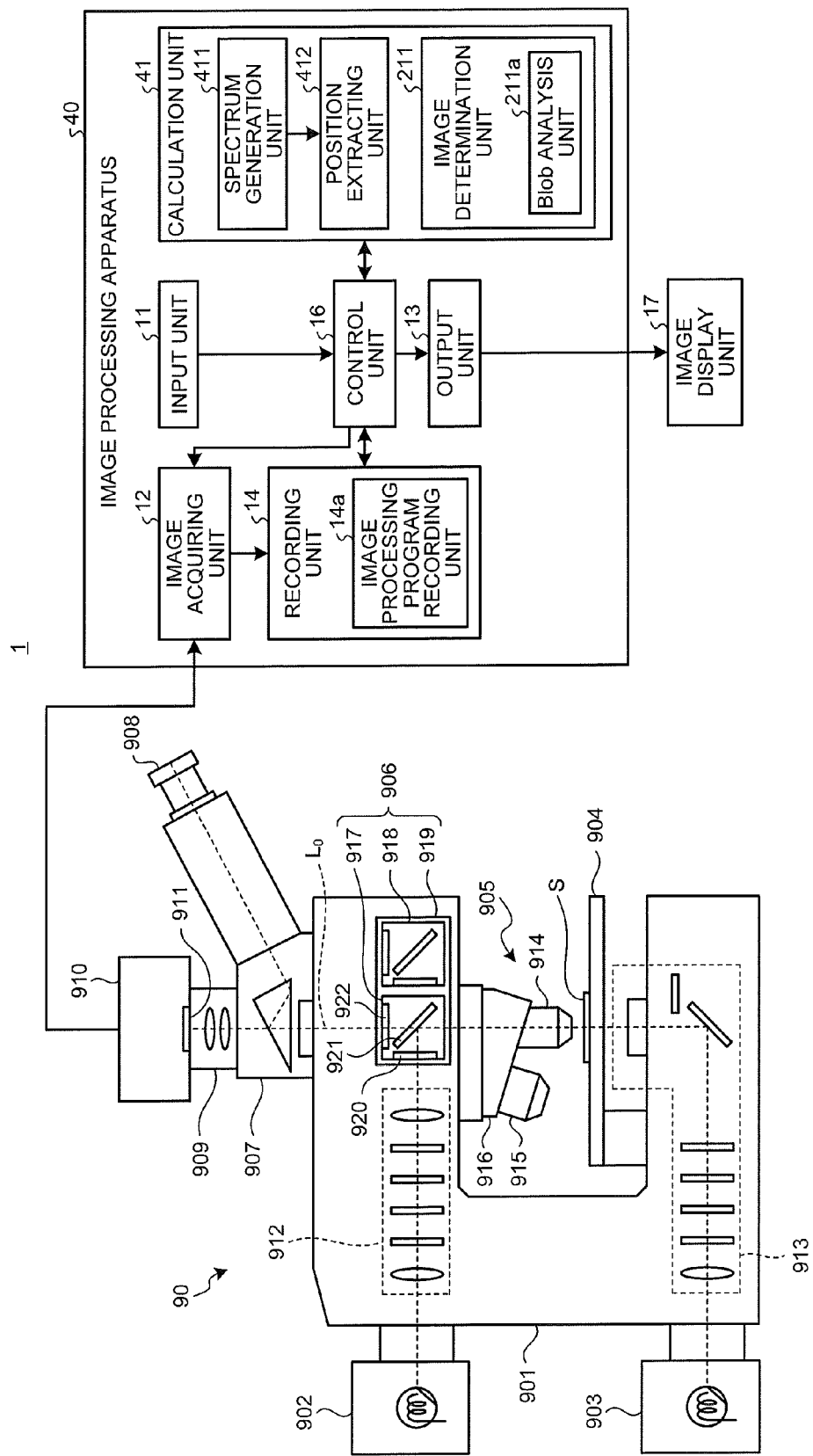
FIG. 24 is a diagram illustrating the configuration of a microscope system according to a fourth embodiment of the present invention.

FIG. 24 is a diagram illustrating a microscope system according to the fourth embodiment of the present invention. As illustrated in FIG. 24, a microscope system 1 according to the fourth embodiment includes a microscope apparatus 90 and an image processing apparatus 40.

The microscope apparatus 90 includes a substantially C-shaped arm section 901, an epi-illumination light source 902 and an epi-illumination optical system 912, and a transmitted-light illumination light source 903 and a transmitted-light illumination optical system 913, which are provided to the arm section 901, a sample stage 904 attached to the arm section 901, an objective lens unit 905 having an objective lens 914 placed, facing the sample stage 904, in an observation optical path $L_O$, a cube unit 906 provided in the observation optical path $L_O$, a trinocular tube unit 907 provided in the observation optical path $L_O$, an eyepiece unit 908 provided via the trinocular tube unit 907, and a tube lens unit 909 coupled to the trinocular tube unit 907. An imaging unit 910 is provided at an end of the tube lens unit 909.

The epi-illumination optical system 912 includes various optical members (such as a filter unit, shutter, field stop, and aperture diaphragm) for concentrating epi-illumination emitted from the epi-illumination light source 902 and guiding the light in the direction of the observation optical path $L_O$. On the other hand, the transmitted-light illumination optical system 913 includes various optical members (such as a collector lens, filter unit, field stop, shutter, aperture diaphragm, condenser optical device unit, and top lent unit) for concentrating transmitted-light illumination emitted from the transmitted-light illumination light source 903 and guiding the light in the direction of the observation optical path $L_O$.

The objective lens unit 905 includes a plurality of objective lenses 914 and 915 each having a different magnification, and a revolver 916 that holds these objective lenses 914 and 915. The revolver 916 is rotated to switch between the objective lenses 914 and 915 and places the objective lens in a position facing the sample stage 904 in the observation optical path $L_O$. Accordingly, the magnification of a microscope observation image can be changed. In FIG. 24, that the objective lens 914 is placed on the observation optical path $L_O$.

The cube unit 906 includes a plurality of optical cubes 917 and 918, and a cube switching portion 919 that holds these optical cubes 917 and 918 in a switchable manner, and switches between the optical cubes 917 and 918 to place the optical cube in the observation optical path $L_O$ according to microscope. For example, when fluorescence observation is performed by the microscope apparatus 90, used is the optical cube (fluorescence cube) 917 in which an excitation filter 920 that selectively transmits light (excitation light) in a specific wavelength band among light emitted from the epi-illumination light source 902 and passing through the epi-illumination optical system 912, a dichroic mirror 921 that reflects the excitation light selected by the excitation filter 920 and transmits fluorescence generated in a specimen S, and an absorption filter 922 that selectively transmits only light (fluorescence) in a specific wavelength band among light incident from the direction of the specimen S are combined in a cube form.

The trinocular tube unit 907 separates observation light from the specimen S incident from the direction of the objective lens 914 into the direction of the eyepiece unit 908 and the direction of the tube lens unit 909. The eyepiece unit 908 is used when a user directly observes the specimen S.

The tube lens unit 909 is provided with a zoom portion including a plurality of zoom lenses and a drive unit (not illustrated) that changes the positions of these zoom lenses. The zoom portion adjusts the positions of the zoom lenses and accordingly enlarges or reduces an imaging target in the imaging field of view.

The imaging unit 910 includes an imaging device such as a CCD, and is configured by a multi-band camera that can capture a color image having pixel levels (pixel values) in a plurality of wavelength bands (bands) different from one another in each pixel. In the fourth embodiment, a multi-band camera that can capture an image in at least three bands within a range from the visible area to the near-infrared area, approximately 400 nm to approximately 900 nm, is used as the imaging unit 910. Preferably, a multi-band camera that can capture an image in a plurality of bands each having a band width of approximately 10 nm is used.

Alternatively, in addition to the multi-band camera, a multi-spectral camera that is provided with, for example, a liquid crystal tunable filter, an acoustic tunable filter, or a plurality of narrow bandpass filters, and that can acquire a multi-spectral image may be adopted as the configuration of the imaging unit 910.

The imaging unit 910 includes a light receiving surface 911 that receives observation light emitted from the objective lens 914 and incident via the tube lens unit 909. The imaging unit 910 converts the observation light incident on the light receiving surface 911 into an electrical signal to generate image data and output the image data to the image processing apparatus 40.

The image processing apparatus 40 includes a calculation unit 41 having a spectrum generation unit 411 and a position extracting unit 412 instead of the fluorescence intensity computation unit 151 illustrated in FIG. 15. The configurations and operations of the respective units of the image processing apparatus 40, other than the spectrum generation unit 411 and the position extracting unit 412, are similar to those of the second embodiment.

The spectrum generation unit 411 generates an optical spectrum of each pixel for a fluorescence observation image of an unstained specimen of a gland duct.

The position extracting unit 412 is a pixel area extracting unit that extracts an area of pixels in which the optical spectrum generated by the spectrum generation unit 411 has a specified characteristic, and outputs its position.

Next, reference will be made to an image processing method according to the fourth embodiment. In the fourth embodiment, after an unstained specimen of a gland duct is created as in the first embodiment, the unstained specimen is irradiated with the excitation light to capture an image with a multi-band camera. Accordingly, a fluorescence observation image including a plurality of wavelength components is generated. At this time, in the fourth embodiment, the wavelength band of the excitation light is set to 300 nm to 400 nm, and the imaging wavelength band is set to 400 nm to 700 nm. In this case, as illustrated in FIG. 3, cells emitting fluorescence are displayed in a different color (wavelength component) from surrounding tissues in the fluorescence observation image.

Figure 25:
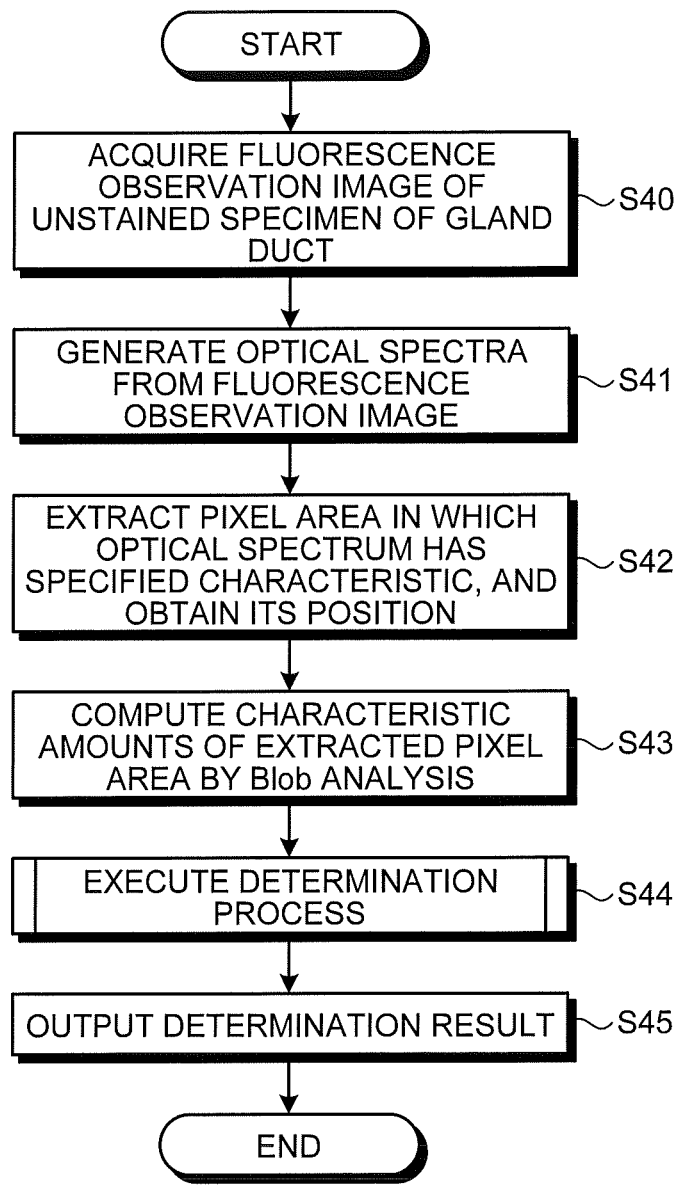
FIG. 25 is a flowchart illustrating the operation of the image processing apparatus illustrated in FIG. 24.

FIG. 25 is a flowchart illustrating the operation of the image processing apparatus 40.

Firstly, in Step S40, the calculation unit 41 acquires a fluorescence observation image including the plurality of wavelength components.

In the following Step S41, the spectrum generation unit 411 generates an optical spectrum of each pixel of the fluorescence observation image.

In Step S42, the position extracting unit 412 extracts a pixel area in which the optical spectrum has the specified characteristic and obtains its position. The characteristic of the optical spectrum is set according to the wavelength band of autofluorescence occurring in a gland duct corresponding to the wavelength band of the excitation light. For example, when the mucosa of the large intestine is irradiated with an ultraviolet light in a wavelength band of 300 nm to 400 nm as the excitation light, green autofluorescence occurs in the mucosa of the large intestine. An optical spectrum across the wavelengths of 480 nm to 700 nm with the peak around 550 nm is observed in the area emitting the green autofluorescence (see FIG. 9). On the other hand, an optical spectrum with the peak around 510 nm is observed in areas of other cells. Hence, an area in which an optical spectrum having high intensity is observed in a wavelength band that is longer than 510 nm and up to approximately 700 nm is extracted and accordingly a cell emitting autofluorescence can be distinguished from other cells.

In Step S43, the blob analysis unit 211a computes characteristic amounts, setting the area extracted by the position extracting unit 412 as a fluorescence area, through blob analysis. The characteristic amounts include, for example, the characteristic amounts (1) to (7) described in the second embodiment. The above characteristic amounts may be obtained by performing the labeling process, and computing shape feature parameters, instead of blob analysis (reference: "Digital gazo syori (Digital Image Processing)", Computer Graphic Arts Society, pp. 181-184).

The following Steps S44 and S45 correspond to Steps S23 and S24 illustrated in FIG. 16. Of them, in Step S44 corresponding to Step S23, FIG. 17 or FIG. 18 is required to be applied depending on the organ including the observation target gland duct.

As described above, according to the fourth embodiment, it is possible to accurately extract a fluorescence area, in other words, an area of a cell emitting autofluorescence in a gland duct, based on the optical spectrum of each pixel of a fluorescence observation image. Hence, it is possible to improve the accuracy of determination of abnormality of the gland duct shown in the fluorescence observation image based on the characteristic amount computed from such a fluorescence area. Therefore, it becomes possible to make a determination on an unstained specimen of the gland duct automatically and more accurately.

Fourth Modification

Next, a fourth modification of the fourth embodiment is described.

Figure 26:
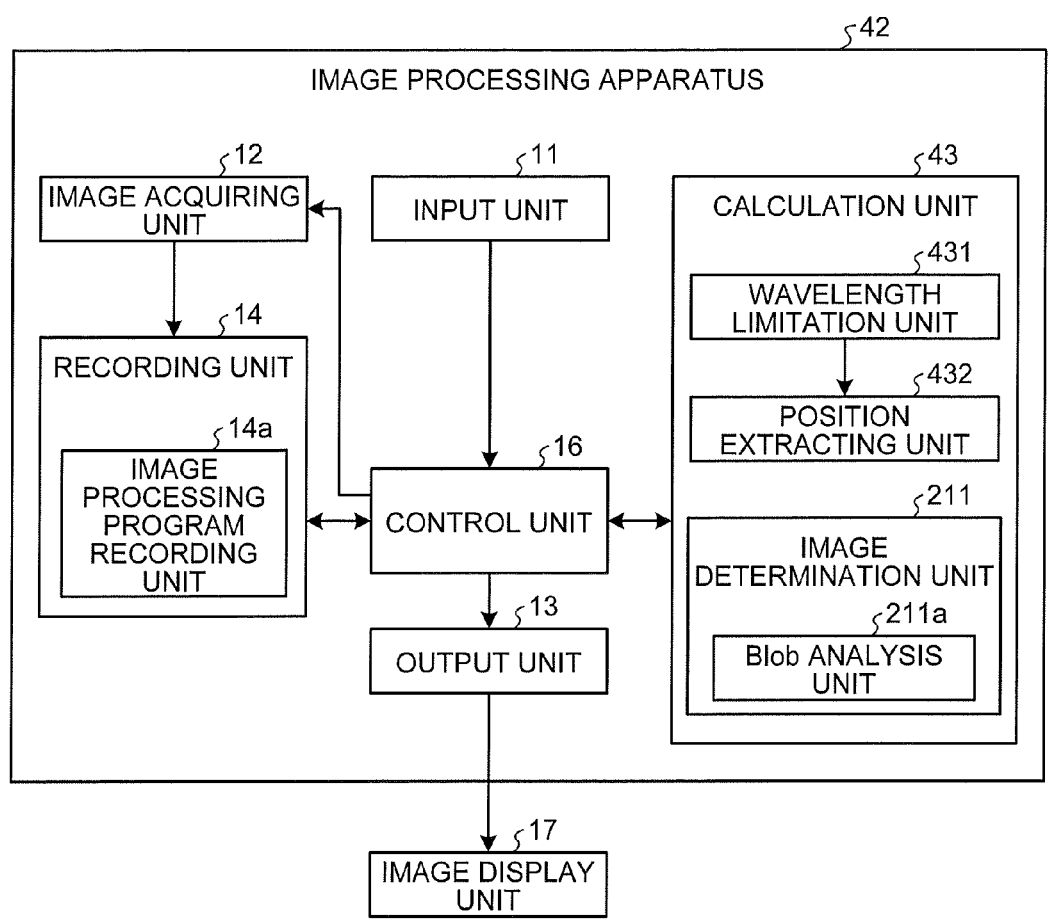
FIG. 26 is a block diagram illustrating the configuration of an image processing apparatus according to a fourth modification of the fourth embodiment of the present invention.

A microscope system according to the fourth modification includes an image processing apparatus 42 illustrated in FIG. 26, instead of the image processing apparatus 40 illustrated in FIG. 24. The configurations and operations of the units of the microscope system according to the fourth modification, other than the image processing apparatus 42, are similar to those of the fourth embodiment.

As illustrated in FIG. 26, the image processing apparatus 42 includes a calculation unit 43 having a wavelength limitation unit 431 and a position extracting unit 432 instead of the spectrum generation unit 411 and the position extracting unit 412, which are illustrated in FIG. 24. The configurations and operations of the units of the image processing apparatus 42, other than the wavelength limitation unit 431 and the position extracting unit 432, are similar to those of the fourth embodiment.

The wavelength limitation unit 431 generates a wavelength limited image being an image where the wavelength component of each pixel is limited to a specified wavelength band, from a fluorescence observation image of an unstained specimen of a gland duct.

The position extracting unit 432 is a pixel area extracting unit that extracts an area of pixels having a specified characteristic from the wavelength limited image, and outputs its position.

Next, reference will be made to an image processing method according to the fourth modification. Also in the fourth modification, an unstained specimen of a gland duct is irradiated with the excitation light in a wavelength band of 300 nm to 400 nm to capture an image with a multi-band camera with an imaging wavelength band of 400 nm to 700 nm, as in the fourth embodiment. Accordingly, a fluorescence observation image including a plurality of wavelength components is generated.

Figure 27:
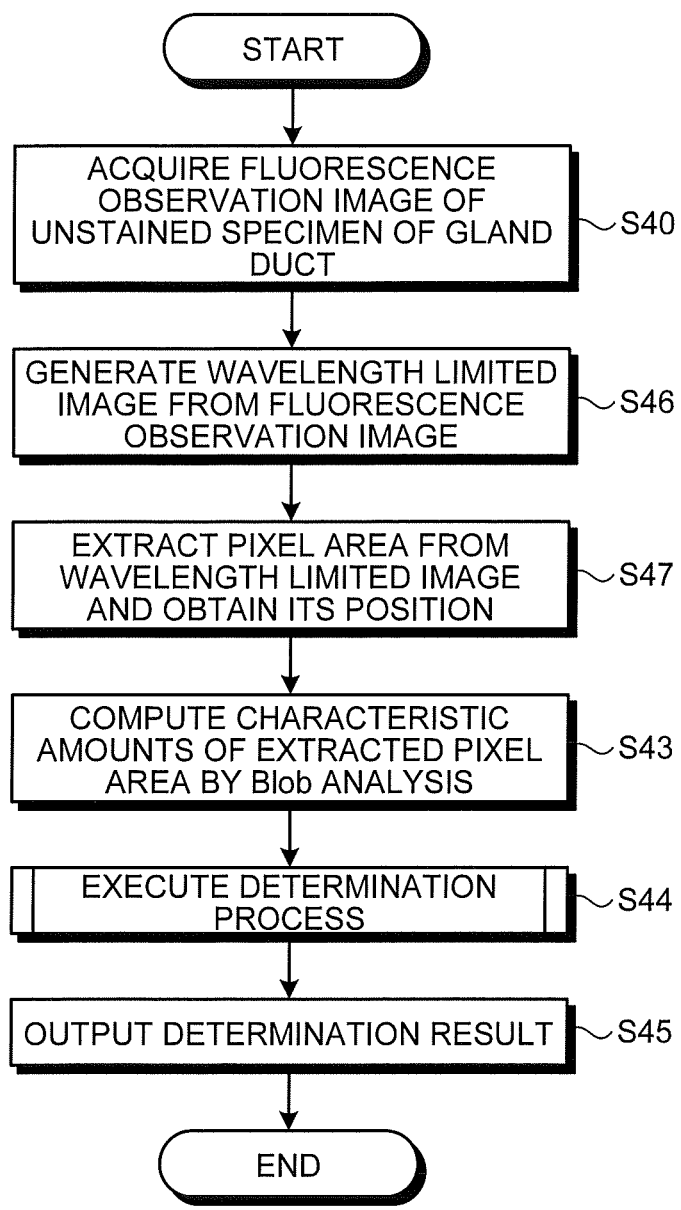
FIG. 27 is a flowchart illustrating the operation of the image processing apparatus illustrated in FIG. 26.

FIG. 27 is a flowchart illustrating the operation of the image processing apparatus 42 according to the fourth modification.

Firstly, in Step S40, the calculation unit 43 acquires a fluorescence observation image including the plurality of wavelength components.

In the following Step S46, the wavelength limitation unit 431 generates an image where the wavelength component of each pixel forming the fluorescence observation image is limited to a specific wavelength band (a wavelength limited image). The band limiting the wavelength is set according to the wavelength band of autofluorescence occurring in the gland duct corresponding to the wavelength band of the excitation light. For example, when the mucosa of the large intestine is irradiated with an ultraviolet light in a wavelength band of 300 nm to 400 nm as the excitation light, green autofluorescence occurs in the mucosa of the large intestine. Hence, the wavelength component of each pixel is limited to a wavelength band longer than 510 nm and equal to or less than 600 nm. Accordingly, it is possible to obtain an image where the area emitting green fluorescence is extracted. Consequently, a cell emitting autofluorescence can be distinguished from other cells, and extracted.

In the following Step S47, the position extracting unit 432 extracts a pixel area having a luminance value that is a specified value or more from the wavelength limited image and obtains its position.

The following Steps S43 to S45 are similar to those of the fourth embodiment.

As described above, according to the fourth modification, it is possible to accurately extract a fluorescence area, in other words, an area of a cell emitting autofluorescence in a gland duct, based on the wavelength component of each pixel of a fluorescence observation image. Hence, it is possible to improve the accuracy of determination of abnormality of the gland duct shown in the fluorescence observation image based on the characteristic amount computed from such a fluorescence area. Therefore, it becomes possible to make a determination on an unstained specimen of the gland duct automatically and more accurately.

Moreover, in the fourth modification, the process of limiting the wavelength for a fluorescence observation image is performed. Accordingly, it is possible to acquire an image equivalent to a fluorescence observation image acquired by providing, for example, a filter that allows a wavelength band of around 510 nm to around 600 nm to pass through on the microscope apparatus 90 side.

For example, a filter that transmits a wavelength band of around 510 nm to 600 nm may be provided on the microscope apparatus 90 side to generate a fluorescence observation image based on the light that passes through the filter among the observation light from the unstained specimen. In this case, a fluorescence observation image where an area emitting green fluorescence is extracted can be obtained without performing the above-mentioned wavelength limited process.

Fifth Embodiment

Next, a fifth embodiment of the present invention is described.

Figure 28:
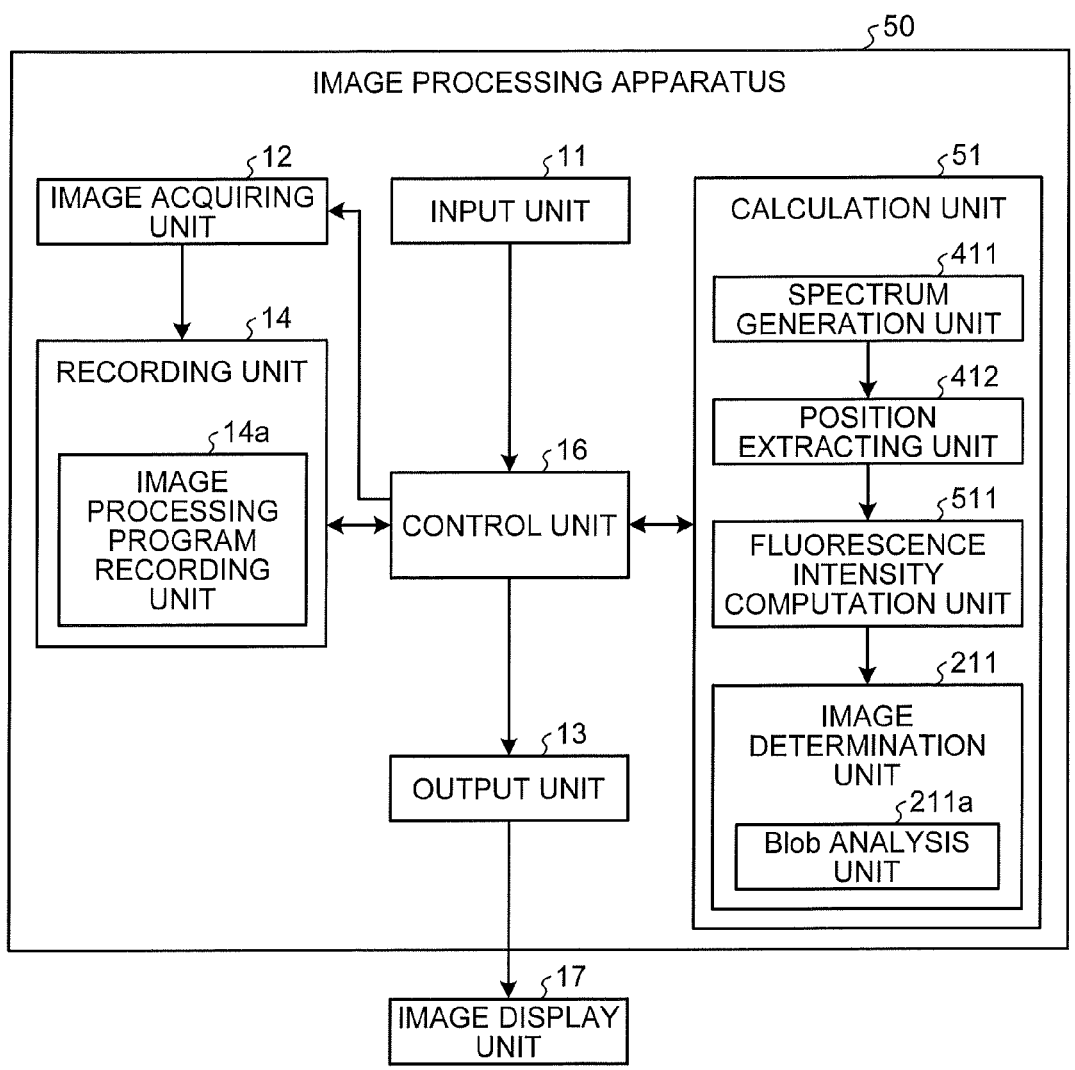
FIG. 28 is a block diagram illustrating the configuration of an image processing apparatus according to a fifth embodiment of the present invention.

A microscope system according to the fifth embodiment includes an image processing apparatus 50 illustrated in FIG. 28, instead of the image processing apparatus 40 illustrated in FIG. 24. The configurations and operations of the units of the microscope system according to the fifth embodiment, other than the image processing apparatus 50, are similar to those of the fourth embodiment.

As illustrated in FIG. 28, the image processing apparatus 50 includes a calculation unit 51 further having a fluorescence intensity computation unit 511, compared with the calculation unit 41 illustrated in FIG. 24. The configuration and operation of the image processing apparatus 50, other than the fluorescence intensity computation unit 511, are similar to those of the fourth embodiment.

The fluorescence intensity computation unit 511 computes the fluorescence intensity (luminance value) of each pixel in the area extracted by the position extracting unit 412.

Figure 29:
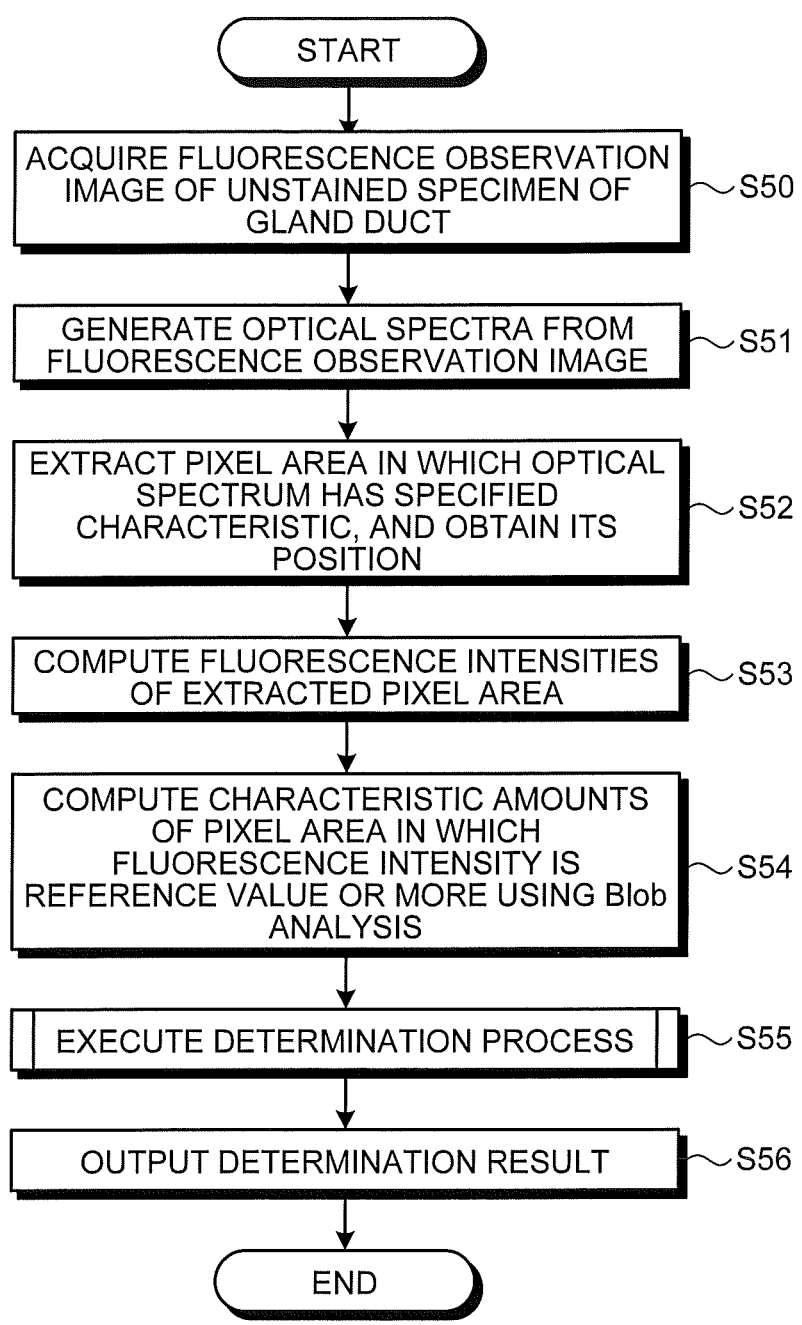
FIG. 29 is a flowchart illustrating the operation of the image processing apparatus illustrated in FIG. 28.

Next, reference will be made to an image processing method according to the fifth embodiment. FIG. 29 is a flowchart illustrating the operation of the image processing apparatus 50. The process is similar to that of the fourth embodiment, until creating an unstained specimen of a gland duct and generating a fluorescence observation image. Moreover, Steps S50 to S52 illustrated in FIG. 29 correspond to Steps S40 to S42 illustrated in FIG. 25.

In Step S53 subsequent to Step S52, the fluorescence intensity computation unit 511 computes fluorescence intensity at each pixel position in the area extracted by the position extracting unit 412. Specifically, the fluorescence intensity computation unit 511 computes the luminance value of each pixel as the fluorescence intensity.

In the following Step S54, the blob analysis unit 211a computes characteristic amounts, setting, as a fluorescence area, an area of pixels in which the fluorescence intensity is a specified reference value or more among the pixels whose fluorescence intensity is computed by the fluorescence intensity computation unit 511. The characteristic amounts include, for example, the characteristic amounts (1) to (7) described in the second embodiment. The above characteristic amounts may be obtained by performing the labeling process, and computing shape feature parameters, instead of blob analysis (reference: "Digital gazo syori (Digital Image Processing)", Computer Graphic Arts Society, pp. 181-184).

The following Steps S55 and S56 correspond to Steps S23 and S24 illustrated in FIG. 16. Of them, in Step S55 corresponding to Step S23, FIG. 17 or 18 is required to be applied depending on the organ including the observation target gland duct.

As described above, according to the fifth embodiment, an area of pixels in which the fluorescence intensity is the specified reference value or more is further extracted from an area of pixels in which the optical spectrum has the specified characteristic. Accordingly, it is possible to further improve the accuracy of extraction of an area of a cell emitting autofluorescence in the gland duct. Hence, a determination is made based on the characteristic amounts of the fluorescence area extracted in this manner and accordingly it is possible to improve the accuracy of determination of abnormality of the gland duct. Therefore, it becomes possible to make a determination on an unstained specimen of the gland duct automatically and more accurately.

Sixth Embodiment

Next, a sixth embodiment of the present invention is described.

Figure 30:
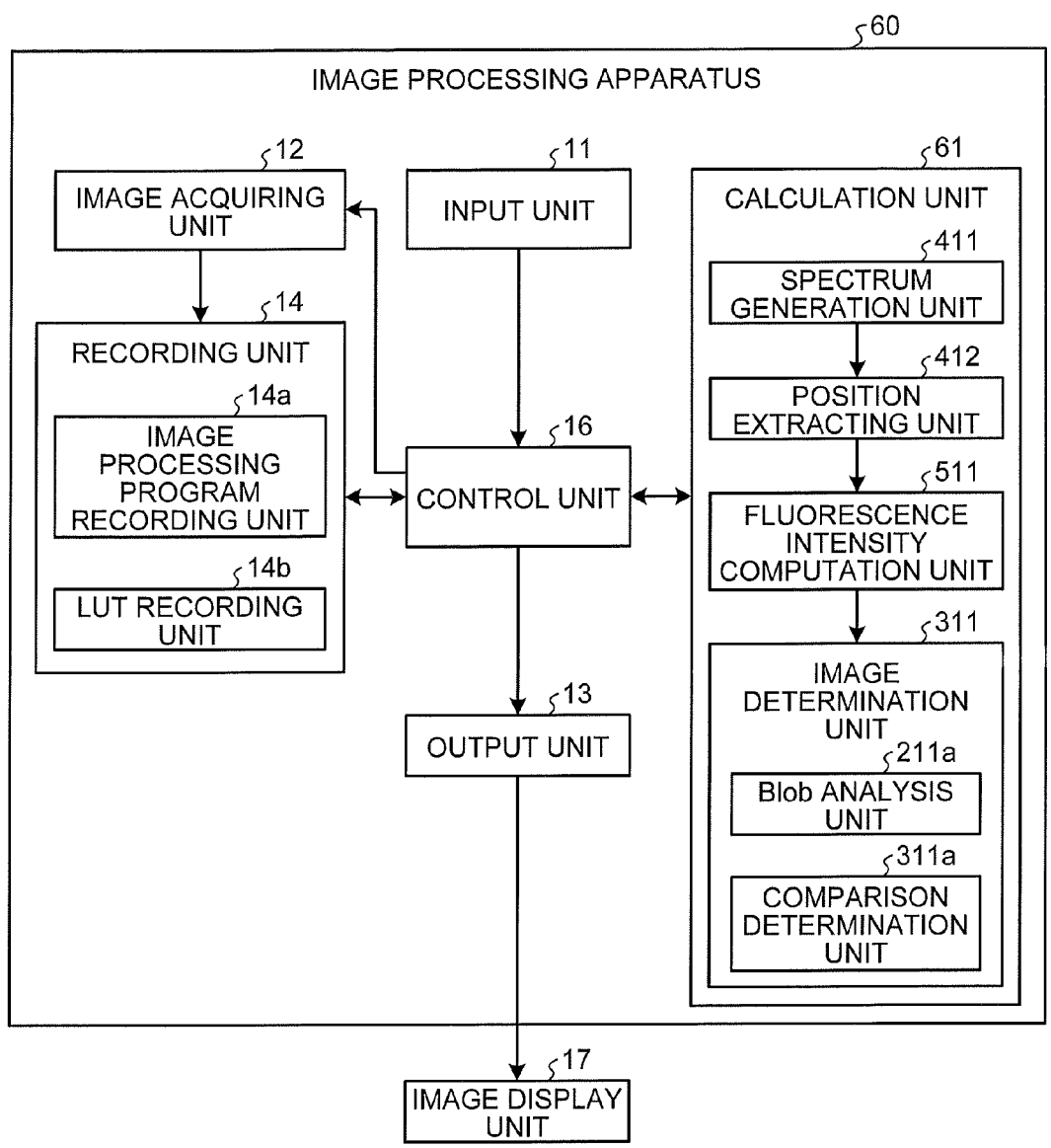
FIG. 30 is a block diagram illustrating the configuration of an image processing apparatus according to a sixth embodiment of the present invention.

A microscope system according to the sixth embodiment includes an image processing apparatus 60 illustrated in FIG. 30, instead of the image processing apparatus 40 illustrated in FIG. 24. The configurations and operations of the units of the microscope system according to the sixth embodiment, other than the image processing apparatus 60, are similar to those of the fourth embodiment.

As illustrated in FIG. 30, the image processing apparatus 60 includes a calculation unit 61 having the image determination unit 311, instead of the image determination unit 211 illustrated in FIG. 28. The configurations and operations of the units of the image processing apparatus 60, other than the image determination unit 311, are similar to those of the fifth embodiment. Moreover, the configuration and operation of the image determination unit 311 are similar to those of the third embodiment. Furthermore, the recording unit 14 includes the LUT recording unit 14b that records lookup tables.

Figure 31:
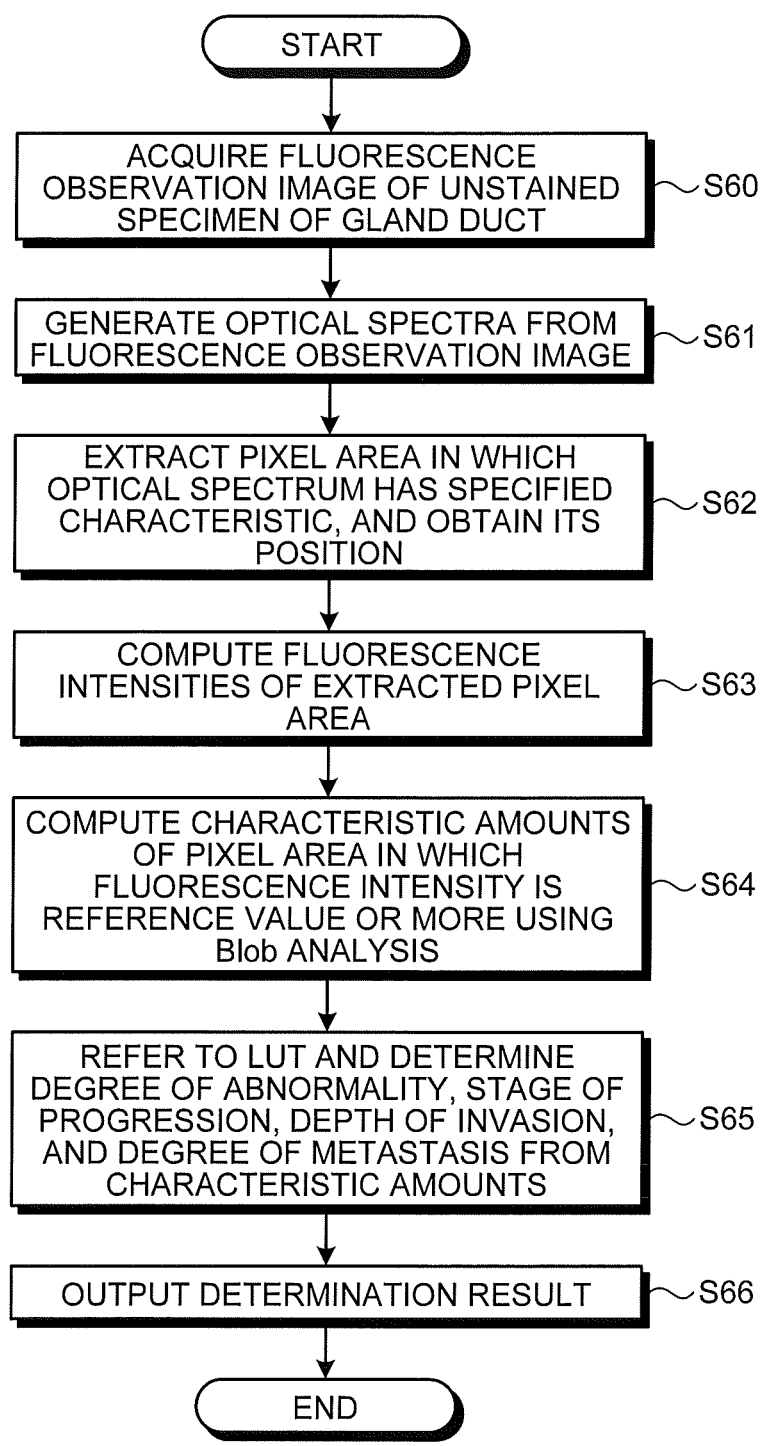
FIG. 31 is a flowchart illustrating the operation of the image processing apparatus illustrated in FIG. 30.

Next, reference will be made to an image processing method according to the sixth embodiment. FIG. 31 is a flowchart illustrating the operation of the image processing apparatus 60. The process is similar to that of the fourth embodiment, until creating an unstained specimen of a gland duct and generating a fluorescence observation image. Moreover, Steps S60 to S64 illustrated in FIG. 31 correspond to Steps S50 to S54 illustrated in FIG. 29.

In Step S65 subsequent to Step S64, the comparison determination unit 311a refers to the lookup tables recorded in the LUT recording unit 14b to determine the state of a lesion, in other words, the degree of abnormality of the gland duct, stage of cancer, depth of cancer invasion, and degree of cancer metastasis, according to the characteristic amounts of the fluorescence area computed by the blob analysis unit 211a. The contents of the lookup tables are similar to those illustrated in the third embodiment (see FIG. 21A to FIG. 21G) or the one illustrated in the third modification (see FIG. 23). The lookup tables are required to be selected and used as appropriate depending on the organ including an observation target gland duct.

In Step S66, the image determination unit 311 outputs the determination result by the comparison determination unit 311a. In response to this, the control unit 16 records the determination result in the recording unit 14 while causing the image display unit 17 to display the determination result. Specifically, the control unit 16 causes the image display unit 17 to display, on the screen, information such as levels of the degree of abnormality of the gland duct, stage of cancer, depth of cancer invasion, and degree of cancer metastasis. Moreover, a processing target fluorescence observation image may also be displayed on the screen to mark and display a fluorescence area (that is, an area of an endocrine cell).

As described above, according to the sixth embodiment, it is possible to accurately extract an area of a cell emitting autofluorescence in a gland duct, based on the optical spectrum and the fluorescence intensity. Therefore, the lookup tables previously created are referred to. Accordingly, it is possible to accurately determine the state of a lesion such as the degree of abnormality of a gland duct, stage of cancer, depth of cancer invasion, and degree of cancer metastasis depending on the characteristic amount. Consequently, it becomes possible to make a determination on an unstained specimen of the gland duct automatically and accurately.

Seventh Embodiment

Next, a seventh embodiment of the present invention is described.

Figure 32:
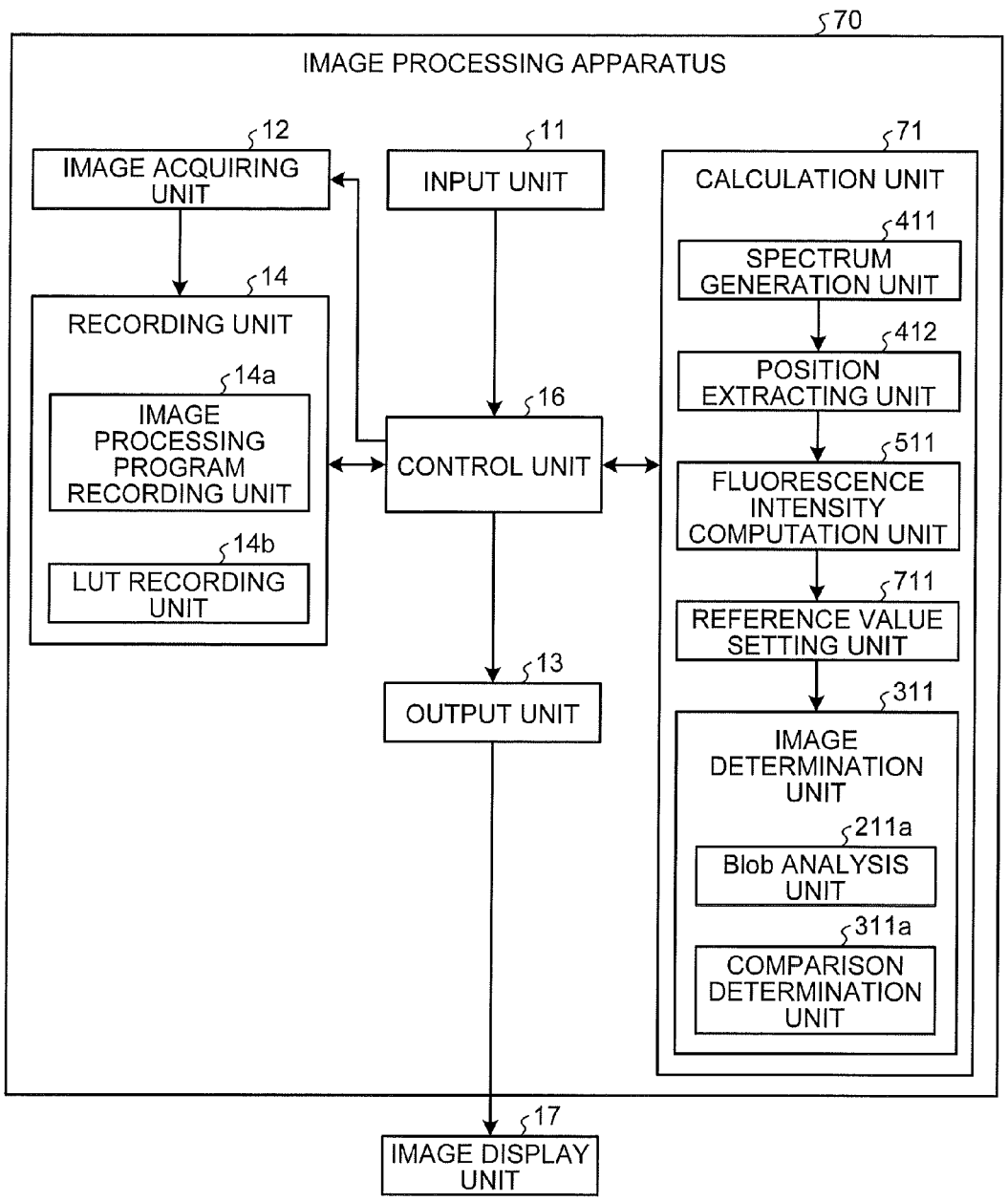
FIG. 32 is a block diagram illustrating the configuration of an image processing apparatus according to a seventh embodiment of the present invention.

A microscope system according to the seventh embodiment includes an image processing apparatus 70 illustrated in FIG. 32, instead of the image processing apparatus 40 illustrated in FIG. 24. The configurations and operations of the units of the microscope system according to the seventh embodiment, other than the image processing apparatus 70, are similar to those of the fourth embodiment.

As illustrated in FIG. 32, the image processing apparatus 70 includes a calculation unit 71 further having a reference value setting unit 711, compared with the calculation unit 61 illustrated in FIG. 30. The configuration and operation of the image processing apparatus 70, other than the reference value setting unit 711, are similar to those of the sixth embodiment.

The reference value setting unit 711 sets a reference value used in the binarization process of blob analysis based on the fluorescence intensity in a processing target fluorescence observation image.

Figure 33:
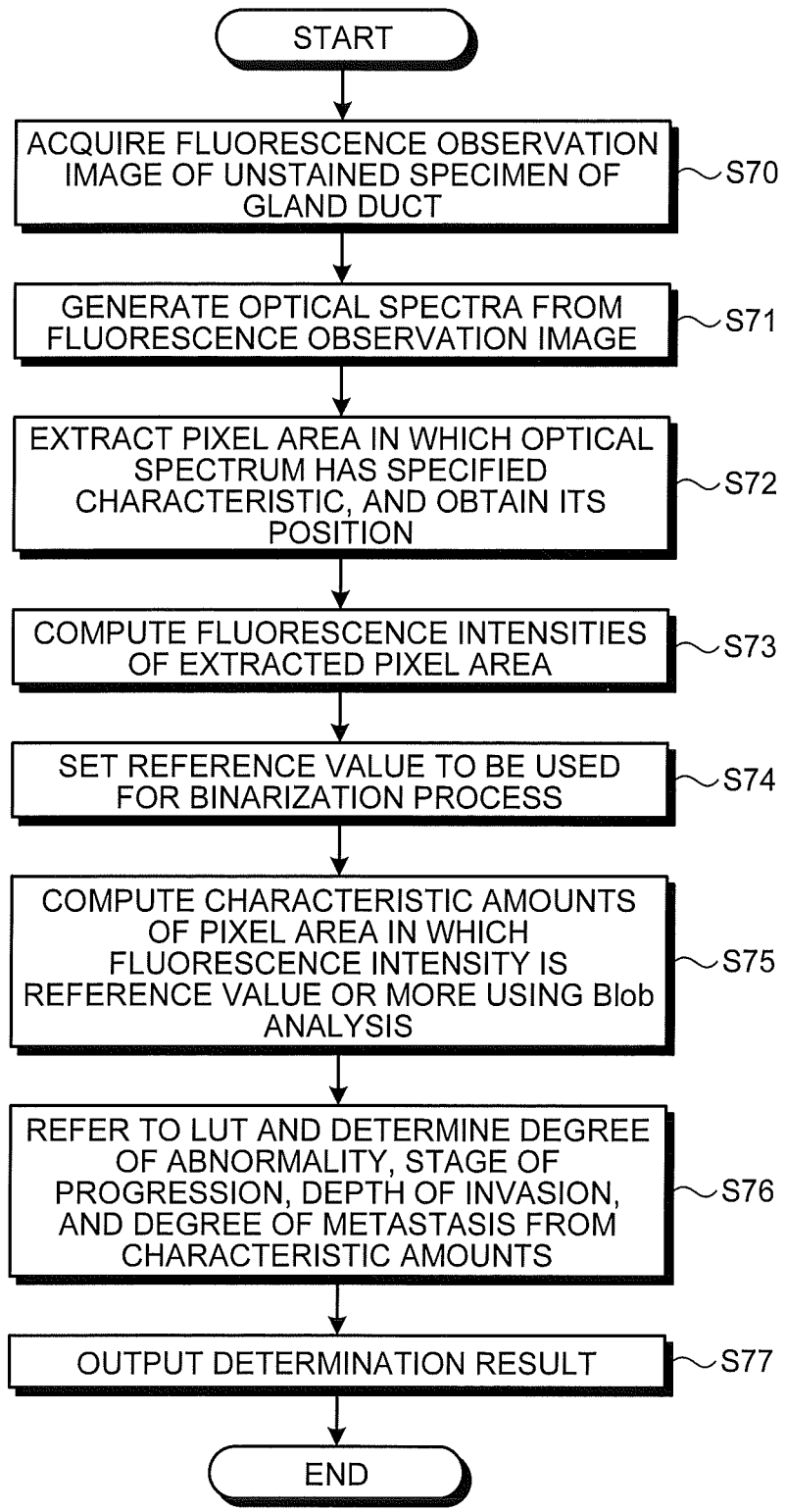
FIG. 33 is a flowchart illustrating the operation of the image processing apparatus illustrated in FIG. 32.

Next, reference will be made to an image processing method according to the seventh embodiment. FIG. 33 is a flowchart illustrating the operation of the image processing apparatus 70. The process is similar to that of the fourth embodiment, until creating an unstained specimen of a gland duct and generating a fluorescence observation image. Moreover, Steps S70 to S73 illustrated in FIG. 33 correspond to Steps S60 to S63 illustrated in FIG. 31.

In Step S74 subsequent to Step S73, the reference value setting unit 711 sets a reference value to be used for the binarization process of a fluorescence intensity image. In other words, the reference value setting unit 711 captures the fluorescence intensity of each pixel computed by the fluorescence intensity computation unit 511, creates a histogram of fluorescence intensities, and computes a reference value from the histogram by a well-known method such as the discriminant analysis method, percentile method, or mode method (reference: "Digital gazo shori (Digital Image Processing)," Computer Graphic Arts Society, pp. 174-176).

The following Steps S75 to S77 are similar to Steps S64 to S66 of FIG. 31. However, in the blob analysis of Step S75, the fluorescence observation image is binarized using the reference value computed in Step S74 to extract a fluorescence area.

As described above, according to the seventh embodiment, the reference value adaptively set based on the fluorescence intensities of a processing target fluorescence observation image is used to binarize the fluorescence observation image. Accordingly, it is possible to improve the accuracy of extraction of an area of a cell emitting autofluorescence in a gland duct. Therefore, it is possible to accurately determine the state of the gland duct such as the degree of abnormality of the gland duct, stage of cancer, depth of cancer invasion, and degree of cancer metastasis by referring to the lookup tables previously created based on the characteristic amount of the extracted area. Consequently, it becomes possible to make a determination on an unstained specimen of the gland duct automatically and accurately.

Eighth Embodiment

Next, an eighth embodiment of the present invention is described.

Figure 34:
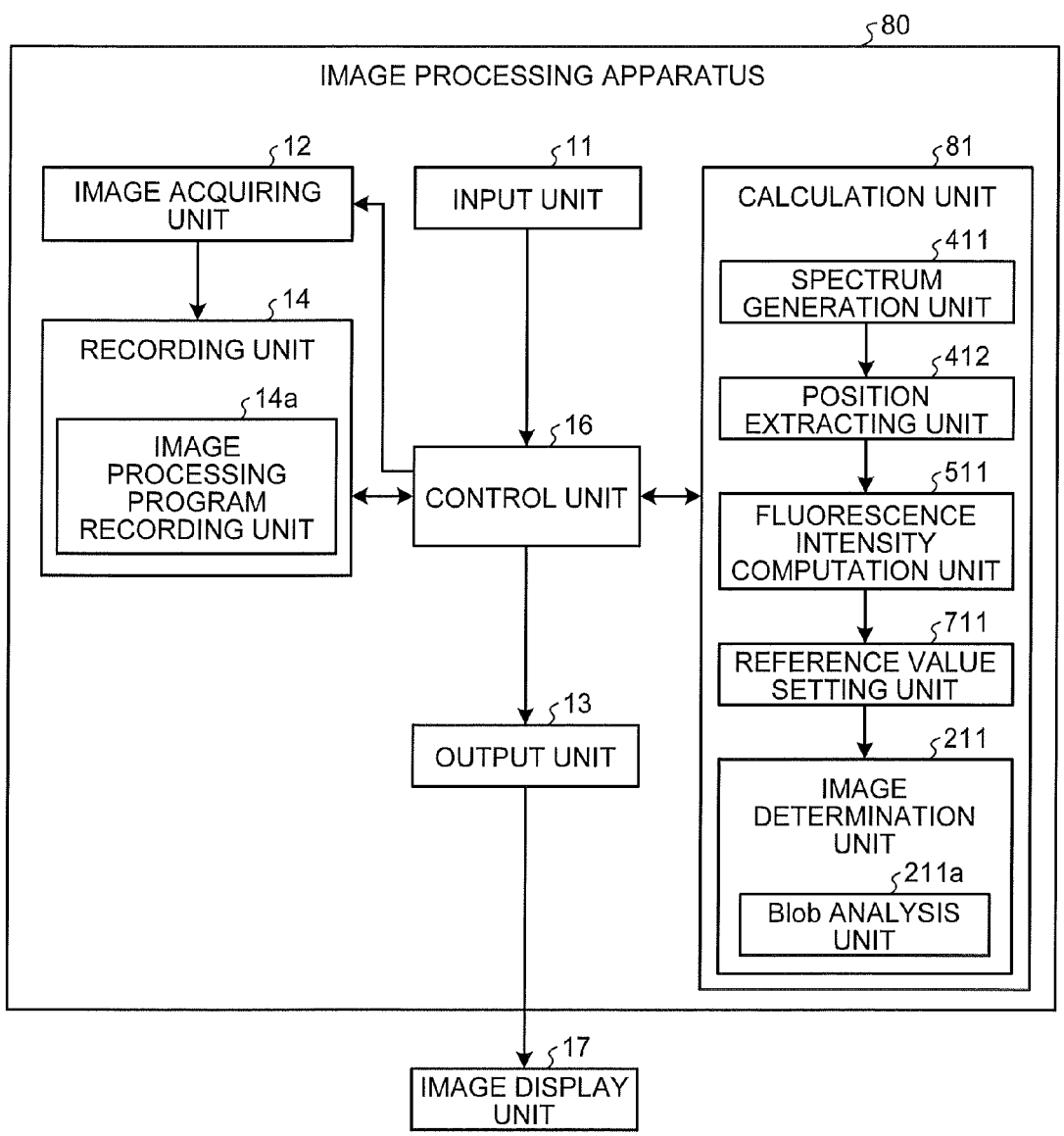
FIG. 34 is a block diagram illustrating the configuration of an image processing apparatus according to an eighth embodiment of the present invention.

A microscope system according to the eighth embodiment includes an image processing apparatus 80 illustrated in FIG. 34, instead of the image processing apparatus 40 illustrated in FIG. 24. The configurations and operations of the units of the microscope system according to the eighth embodiment, other than the image processing apparatus 80, are similar to those of the fourth embodiment.

As illustrated in FIG. 34, the image processing apparatus 80 includes a calculation unit 81 having the image determination unit 211, instead of the image determination unit 311 illustrated in FIG. 32. The configuration and operation of the image processing apparatus 80, other than the image determination unit 211, are similar to those of the seventh embodiment. Moreover, the configuration and operation of the image determination unit 211 are similar to those of the second embodiment.

Figure 35:
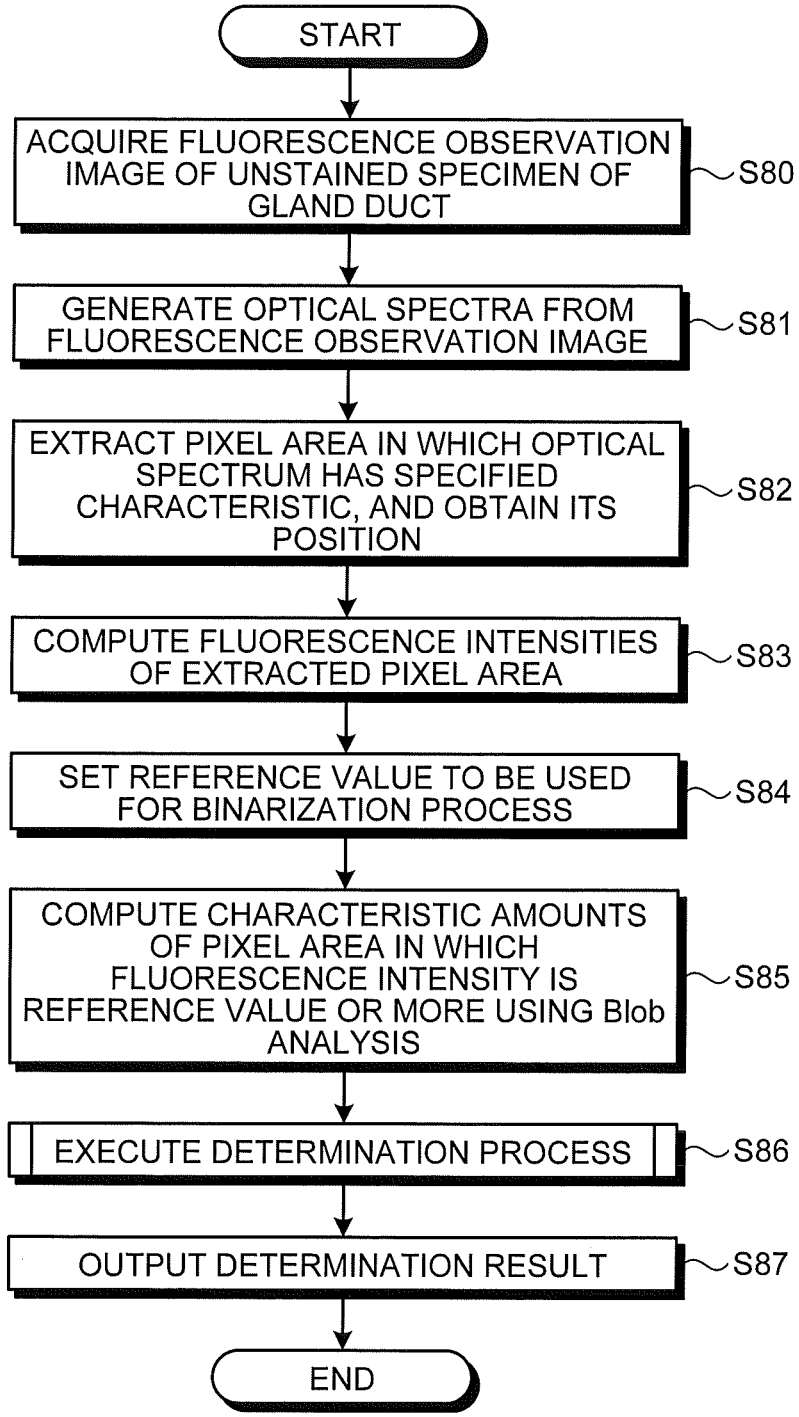
FIG. 35 is a flowchart illustrating the operation of the image processing apparatus illustrated in FIG. 34.

Next, reference will be made to an image processing method according to the eighth embodiment. FIG. 35 is a flowchart illustrating the operation of the image processing apparatus 80. The process is similar to that of the fourth embodiment, until creating an unstained specimen of a gland duct and generating a fluorescence observation image. Moreover, Steps S80 to S85 illustrated in FIG. 35 correspond to Steps S70 to S75 illustrated in FIG. 33. In other words, in the eighth embodiment, the reference value set based on the fluorescence intensities of a fluorescence observation image is used to binarize the fluorescence observation image. Characteristic amounts are computed for a fluorescence area extracted from a binary image generated as a consequence of the binarization.

The following Steps S86 and S87 are similar to Steps S23 and S24 of FIG. 16. In other words, the image determination unit 211 determines, based on a comparison between the characteristic amounts and the threshold values, whether or not the gland duct shown in the fluorescence observation image has an abnormality. Of them, in Step S86 corresponding to Step S23, FIG. 17 or FIG. 18 is required to be applied depending on the organ including the observation target gland duct.

As described above, according to the eighth embodiment, the reference value adaptively set based on the fluorescence intensities of a processing target fluorescence observation image is used to binarize the fluorescence observation image. Accordingly, it is possible to improve the accuracy of extraction of an area of a cell emitting autofluorescence in the gland duct. Therefore, it becomes possible to improve the accuracy of determination on the presence or absence of an abnormality of the gland duct shown in the fluorescence observation image based on the characteristic amounts of the area extracted in this manner.

Ninth Embodiment

Next, a ninth embodiment of the present invention is described.

Figure 36:
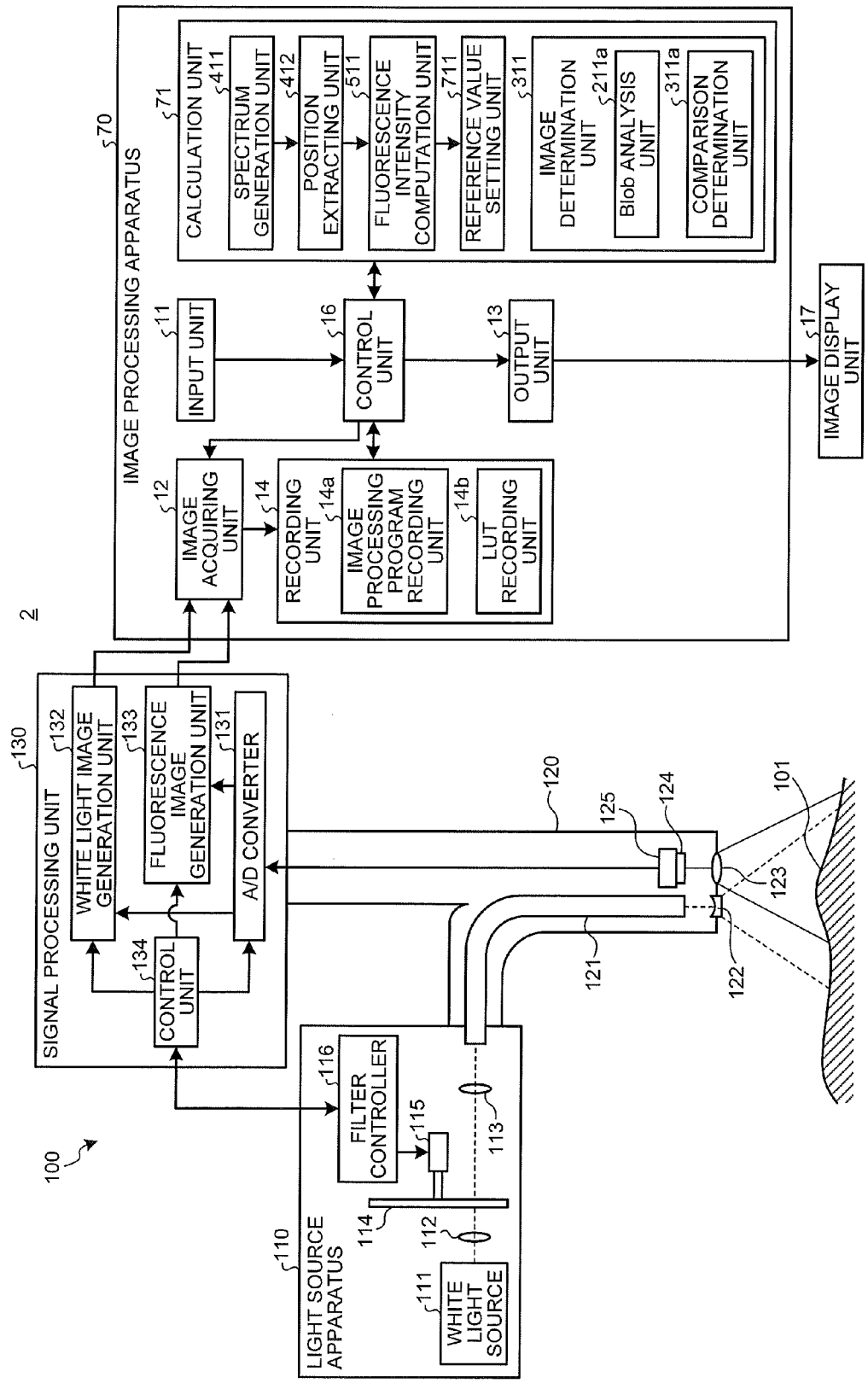
FIG. 36 is a diagram illustrating the configuration of an endoscope system according to a ninth embodiment of the present invention.

FIG. 36 is a diagram illustrating the configuration of an endoscope system according to the ninth embodiment. As illustrated in FIG. 36, an endoscope system 2 according to the ninth embodiment includes an endoscope apparatus 100 and the image processing apparatus 70. Moreover, the configuration and operation of the image processing apparatus 70 are similar to those of the seventh embodiment.

The endoscope apparatus 100 includes a light source apparatus 110 that generates light to irradiate the inside of a subject, a long slender insertion section 120 that is inserted into the body cavity of the subject, captures the inside of the subject (for example, a gland duct 101), and acquires an image signal, and a signal processing unit 130 that generates an image of the inside of the subject based on the image signal acquired by the insertion section 120.

The light source apparatus 110 functions as a light source unit that switches between excitation light that excites the gland duct 101 and white light being an example of ordinary light, and irradiates the gland duct 101 with the light. Specifically, the light source apparatus 110 includes a white light source 111, a collimator lens 112 that substantially collimates light emitted from the white light source 111, a condenser lens 113 that collects the collimated light, a rotary filter 114 that switches light to irradiate the gland duct 101 to the excitation light or the white light, a motor 115 being a driving source of the rotary filter 114, and a filter controller 116 that controls the rotary filter 114.

The white light source 111 is configured by a light emitting source that can emit light in a wide band of, for example, around 250 nm to around 1100 nm, like a xenon lamp, and emits the white light based on a switch operation on the light source apparatus 110 from the outside. The collimator lens 112 is placed on an optical path of the white light emitted from the white light source 111, and substantially collimates the white light emitted from the white light source 111. The light collimated by the collimator lens 112 passes through the rotary filter 114, and is then collected by the condenser lens 113. The light collected by the condenser lens 113 is applied to the gland duct 101 via the insertion section 120.

The rotary filter 114 includes a white light filter and an excitation light filter, which are different in spectral characteristics from each other, and extracts a light in a specified wavelength band from the white light emitted from the white light source 111. More specifically, the white light filter transmits a white light in a wavelength band of, for example, 420 nm to 650 nm among the white light emitted from the white light source 111. On the other hand, the excitation light filter transmits an excitation light in a wavelength band of, for example, 300 nm to 400 nm among the white light emitted from the white light source 111. The excitation light that passes through the excitation light filter excites the unstained gland duct 101, and generates fluorescence in a wavelength band of, for example, 400 nm to 700 nm indicating the existence of an endocrine cell.

The rotary filter 114 receives the driving force of the motor 115 to rotate in the circumferential direction. Accordingly, the white light filter and the excitation light filter are sequentially switched to be placed on the optical path (see a broken line in the light source apparatus 110 illustrated in FIG. 36) of the white light emitted from the white light source 111. In other words, the rotary filter 114 transmits a white light, at 420 nm to 650 nm in a state where the white light filter is placed on the optical path, and transmits the excitation light at 300 nm to 400 nm in a state where the excitation light filter is placed on the optical path. Consequently, the white light and excitation light are alternatingly emitted from the light source apparatus 110 in given cycles.

The filter controller 116 controls the switching of the filter in the optical path by the rotation of the above-mentioned rotary filter 114. Specifically, the filter controller 116 controls the rotation and drive of the motor 115 connected to the rotary filter 114 via a rotation shaft, and controls the rotation and drive of the rotary filter 114 through the drive control of the motor 115. Consequently, the filter controller 116 alternatingly places the white light filter and the excitation light filter in the optical path of the white light emitted from the white light source 111. In this manner, the filter controller 116 controls the filter switching of the rotary filter 114 in the optical path. Moreover, the filter controller 116 grasps which of the white light filter and the excitation light filter is placed on the optical path, based on the rotary drive state such as the number of revolutions of the motor 115. The filter controller 116 transmits, to the signal processing unit 130, filter information indicating the filter placed on the optical path. The operation of the filter controller 116 is controlled by a control unit 134 of the signal processing unit 130 described below.

The insertion section 120 is a long slender flexible structure that can be inserted into the body cavity of a subject, and can bend in a desired direction based on an operation of an operating unit provided to the endoscope apparatus 100. Moreover, a proximal end side of the insertion section 120 is connected to the light source apparatus 110 and the signal processing unit 130.

The insertion section 120 includes a light guide fiber 121 that guides the light emitted from the light source apparatus 110 to a distal end side, and a lens 122 that diffuses the light guided by the light guide fiber 121. Moreover, the insertion section 120 includes an objective lens 123 that collects ordinary light or fluorescence from the gland duct 101, and an imaging unit 125 that captures the gland duct 101 being a subject, and generates an image signal. The imaging unit 125 is provided with a color filter group 124 including a plurality of color filters having different spectral characteristics.

The light guide fiber 121 is configured using an optical fiber or the like, and sequentially propagates the white light and the excitation light alternatingly emitted from the above-mentioned light source apparatus 110 to the distal end side of the insertion section 120. The white light and the excitation light from the light source apparatus 110, which are sequentially guided by the light guide fiber 121, are sequentially diffused by the lens 122, and alternatingly applied to the gland duct 101.

Here, when endocrine cells exist in the gland duct 101, the excitation light from the light source apparatus 110, which is applied to the gland duct 101, excites the endocrine cells, and causes fluorescence to occur having a peak in, for example, a wavelength band that is longer than 510 nm and up to approximately 600 nm. On the other hand, when the white light from the light source apparatus 110 is applied to the gland duct 101, the ordinary light (white light) is reflected from the gland duct 101.

The objective lens 123 collects the white light reflected from the gland duct 101 when the white light from the light source apparatus 110 is applied to the gland duct 101. On the other hand, the objective lens 123 collects fluorescence generated from the gland duct 101 and the excitation light reflected from the gland duct 101 when the excitation light from the light source apparatus 110 is applied to the gland duct 101.

The color filter group 124 includes the plurality of color filters having different spectral characteristics, and separates the white light from the gland duct 101 into lights of the respective color components for each pixel of the imaging unit 125, and transmits the lights of the color components toward each pixel of the imaging unit 125. The color filter group 124 is primary color filters being, for example, a mosaic of pluralities of red light filters (R) being color filters that transmit a red light, green light filters (G) being color filters that transmit a green light, and blue light filters (B) being color filters that transmit a blue light.

The color filter group 124 having such a configuration extracts a blue light at, for example, 430 to 480 nm by the blue light filters, extracts a green light at, for example, 510 to 580 nm by the green light filters, and extracts a red light at, for example, 600 to 680 nm by the red light filters, from the light from the gland duct 101, which passes through the objective lens 123. The blue light filters in the color filter group 124 transmit a blue component of the white light toward pixels of the imaging unit 125 corresponding to blue. The green light filters in the color filter group 124 transmit a green component of the white light toward pixels of the imaging unit 125 corresponding to green. The red light filters in the color filter group 124 transmit a red component of the white light toward pixels of the imaging unit 125 corresponding to red.

The imaging unit 125 is configured using, for example, a Bayer color imaging device in which each color filter having a different spectral characteristic is placed in each pixel in a light receiving surface. Specifically, the imaging unit 125 includes, on the light receiving surface, an ultraviolet-cut off filter that removes an ultraviolet light at wavelengths of 400 nm or less and the above-mentioned color filter group 124. A light receiving unit of the imaging unit 125 sets, for example, a pixel aggregate of 2×2 as a basic unit, and is formed of a pixel group including a plurality of pixel aggregates. In the light receiving unit of the imaging unit 125, a color filter aggregate being a basic unit of the above-mentioned color filter group 124 is placed for each pixel aggregate of the basic unit. In other words, the imaging unit 125 includes, on the pixel aggregate being the basic unit, one or more red light filters, one or more green light filters, and one or more blue light filters of a color filter aggregate being the basic unit of the color filter group 124.

The imaging unit 125 having such a configuration receives the light (the white light or fluorescence) from the gland duct 101, the light passing through the objective lens 123, via the above-mentioned color filter group 124 and the like. Consequently, the imaging unit 125 performs a photoelectric conversion process by each pixel in the pixel group on the ordinary light of each color component separated by the color filter group 124, and generates an image signal of each color component forming an image of the gland duct 101.

The signal processing unit 130 processes the image signal generated by the imaging unit 125, generates image data, and outputs the image data to the image processing apparatus 70. Specifically, the signal processing unit 130 includes an A/D converter 131 that converts each analog image signal output from the imaging unit 125 into a digital signal, and a white light image generation unit 132 that generates a white light image of the gland duct 101 based on the image signal (image data) converted into the digital signal, a fluorescence image generation unit 133 that generates a fluorescence image of the gland duct 101 based on the image signal, and the control unit 134 that controls these respective units.

The A/D converter 131 sequentially captures image signals output from the imaging unit 125 into digital signals, and outputs the digital signals alternatingly to the white light image generation unit 132 and the fluorescence image generation unit 133 under the control of the control unit 134. Specifically, the A/D converter 131 converts the image signals of each color captured from the imaging unit 125 into digital signals while the light source apparatus 110 is emitting the white light, and then sequentially outputs the digital signals to the white light image generation unit 132. On the other hand, the A/D converter 131 converts the images signals of each color captured from the imaging unit 125 into digital signals while the light source apparatus 110 is emitting the excitation light, and then sequentially outputs the digital signals to the fluorescence image generation unit 133.

The white light image generation unit 132 temporarily stores the image signals of each color input from the A/D converter 131 and generates a white light image of the gland duct 101 based on one frame worth of image signals. Specifically, the white light image generation unit 132 accumulates B image signals, G image signals, and R image signals in a single-plate state corresponding to one frame worth of a white light image, performs an interpolation process on the B, G, and R image signals in the single-plate state, and accordingly generates a three-plate image signal in which the color components are synthesized, for each pixel aggregate being the basic unit. The white light image generation unit 132 performs a color conversion process, a gray level conversion process, and the like on each three-plate image signal generated in this manner, generates a white light image of the gland duct 101, and outputs the white light image to the image processing apparatus 70.

The fluorescence image generation unit 133 temporarily stores G image signals including a wavelength component of fluorescence generated from the gland duct 101 among the image signals of the colors input from the A/D converter 131, generates a fluorescence image of the gland duct 101 based on one frame worth of image signals, and outputs the fluorescence image to the image processing apparatus 70.

The control unit 134 performs control such that a timing when the light source apparatus 110 applies the white or excitation light to the gland duct 101, and a timing when the imaging unit 125 captures an image are synchronized, and image data of a white light image and image data of a fluorescence image are separated and acquired. Specifically, the control unit 134 sequentially acquires filter information from the filter controller 116, and identifies the filter of the rotary filter 114 currently placed on the optical path of the light source apparatus 110 between the white light filter and the excitation light filter, based on the filter information. The control unit 134 then controls the A/D converter 131 such that an image signal converted into a digital signal is output to the white light image generation unit 132 if the filter placed on the optical path is the white light filter. On the other hand, the control unit 134 controls the A/D converter 131 such that an image signal converted into a digital signal is output to the fluorescence image generation unit 133 if the filter placed on the optical path is the excitation light filter.

The white light image and the fluorescence image, which are output from such an endoscope apparatus 100, are input into the image processing apparatus 70 and recorded in the recording unit 14. In the image processing apparatus 70, the calculation unit 71 performs the determination process (determination on the presence or absence of an abnormality of a gland duct) as in the above-mentioned seventh embodiment, based on the fluorescence image among the images recorded in the recording unit 14. The control unit 16 causes the image display unit 17 to display the result of the determination process while reading the white light image recorded in the recording unit 14, superimposing a pixel area (an area of an endocrine cell) extracted by the calculation unit 71 on the white light image, and causing the image display unit 17 to display the white light image.

The above-mentioned configuration of the endoscope apparatus 100 is an example. An endoscope system can be configured combining various well-known endoscope apparatuses with the image processing apparatus 70. Moreover, the image processing apparatus 10, 20, 30, 40, 42, 50, 60, or 80 described in the embodiments, instead of the image processing apparatus 70, may be combined with an endoscope apparatus to configure the endoscope system.

According to some embodiments, a value corresponding to intensity of fluorescence is computed as fluorescence intensity from a fluorescence observation image of a gland duct. Whether or not an endocrine cell exists in the gland duct is determined based on the fluorescence intensity. The abnormality of the gland duct is determined based on the determination result of the endocrine cell. Accordingly, it is possible to easily and stably determine the abnormality and the like of a living body based on an observation image of the living body acquired without staining.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An image processing apparatus comprising:
an image acquiring interface configured to acquire image information representing an image acquired by irradiating a gland duct with excitation light and observing fluorescence generated in the gland duct; and
a processor comprising hardware, wherein the processor is configured to:
compute a value corresponding to intensity of the fluorescence as fluorescence intensity based on the image information; and
determine whether or not an endocrine cell exists in the gland duct based on the fluorescence intensity computed, and determine abnormality of the gland duct based on a determination result of the endocrine cell.

2. The image processing apparatus according to claim 1, wherein the processor is configured to compute a luminance value of each pixel in the image, as the value corresponding to intensity of the fluorescence.

3. The image processing apparatus according to claim 1, wherein the processor is configured to compare fluorescence intensities of pixels in the image, or a total value or representative value of the fluorescence intensities of the pixels in the image, with a specified reference value, and accordingly determine whether or not the endocrine cell exists in the gland duct.

4. The image processing apparatus according to claim 1, wherein the processor is configured to extract, from the image, areas each including a plurality of pixels in which the fluorescence intensity is a specified reference value or more, and to determine whether or not the endocrine cell exists in the gland duct based on a characteristic amount of each of the areas.

5. The image processing apparatus according to claim 4, wherein the processor is configured to binarize the image based on the fluorescence intensity and accordingly extract the area.

6. The image processing apparatus according to claim 5, wherein the processor is configured to set a reference value in binarizing the image, based on the fluorescence intensity of each pixel in the image.

7. The image processing apparatus according to claim 4, wherein the processor is configured to compute the characteristic amount of each of the areas using at least any one of an area or fluorescence intensity of each of the areas, the number of the areas, and perimeter, circumscribed distance, or roundness of each of the areas.

8. The image processing apparatus according to claim 1, wherein the processor is configured to:
generate an optical spectrum of each pixel in the image;
extract an area of pixels in which the optical spectrum has a specified characteristic; and
compute the fluorescence intensity for the area extracted.

9. An image processing apparatus comprising:
an image acquiring interface configured to acquire image information representing an image acquired by irradiating a gland duct with excitation light and observing fluorescence generated in the gland duct; and
a processor comprising hardware, wherein the processor is configured to:
generate an optical spectrum of each pixel in the image based on the image information;
extract an area of pixels in which the optical spectrum has a specified characteristic; and
determine whether or not an endocrine cell exists in the gland duct based on a characteristic amount of the area extracted, and determine abnormality of the gland duct based on a determination result of the endocrine cell.

10. The image processing apparatus according to claim 8, wherein a wavelength band of the excitation light is 300 nm or more and 400 nm or less, and
wherein the processor is configured to extract an area of pixels in which the optical spectrum is observed in a wavelength band of 480 nm or more and 700 nm or less.

11. An image processing apparatus comprising:
an image acquiring interface configured to acquire image information representing an image acquired by irradiating a gland duct with excitation light and observing fluorescence generated in the gland duct; and a processor comprising hardware, wherein the processor is configured to:
  generate a wavelength limited image in which a wavelength component of each pixel in the image is limited to a specified wavelength band;
  extract an area of pixels having a luminance value that is a specified value or more from the wavelength limited image; and
  determine whether or not an endocrine cell exists in the gland duct based on a characteristic amount of the area extracted, and determine abnormality of the gland duct based on a determination result of the endocrine cell.

12. The image processing apparatus according to claim 1,
wherein the gland duct is a gland duct of an organ of any one of stomach, small intestine, large intestine, and prostate gland, and
wherein upon determining that no endocrine cell exists in the gland duct or the number of endocrine cells existing in the gland duct is smaller than a specified number, the the processor is configured to determine that the gland duct has an abnormality.

13. The image processing apparatus according to claim 1,
wherein the gland duct is a gland duct of esophagus, and
wherein upon determining that an endocrine cell exists in the gland duct, the processor is configured to determine the gland duct has an abnormality.

14. The image processing apparatus according to claim 4, further comprising a memory configured to record a lookup table in which the characteristic amount of each of the areas is associated with at least one of degree of abnormality, stage of cancer, depth of cancer invasion, and degree of cancer metastasis in the gland duct,
wherein the processor is configured to refer to the lookup table, and to determine at least one of the degree of abnormality, stage of cancer, depth of cancer invasion, and degree of cancer metastasis according to the characteristic amount of each of the areas.

15. The image processing apparatus according to claim 1, wherein the gland duct is unstained.

16. A microscope system comprising:
the image processing apparatus according to claim 1;
a stage on which a specimen is to be placed;
an illumination optical system configured to apply excitation light to the stage;
an objective optical system provided facing the stage to allow light from a direction of the specimen to be incident thereon; and
an imaging sensor configured to capture observation light of the specimen which has passed through the objective optical system, and to generate image information.

17. The microscope system according to claim 16,
wherein the imaging sensor is configured to capture an image in a plurality of wavelength bands different from one another.

18. An endoscope system comprising:
the image processing apparatus according to claim 1;
an illumination optical system configured to apply excitation light to a specimen;
an objective optical system provided facing the specimen to allow light from a direction of the specimen to be incident thereon; and
an imaging sensor configured to capture observation light of the specimen which has passed through the objective optical system, and to generate image information.

19. An image processing method comprising:
acquiring image information representing an image acquired by irradiating a gland duct with excitation light and by observing fluorescence generated in the gland duct;
computing a value corresponding to intensity of the fluorescence as fluorescence intensity based on the image information; and
determining whether or not an endocrine cell exists in the gland duct based on the fluorescence intensity computed, and determining abnormality of the gland duct based on a determination result of the endocrine cell.

* * * * *